(12) United States Patent
Chan et al.

(10) Patent No.: US 7,421,753 B2
(45) Date of Patent: Sep. 9, 2008

(54) ELECTRIC TOOTHBRUSHES

(75) Inventors: John Geoffrey Chan, Loveland, OH (US); Patrick William Brown, Auburn, OH (US); Donald Clarence Fuchs, Jr., Mentor, OH (US); Douglas Alan Gall, Strongsville, OH (US); Trevor Leslie Jackson, Kirtland, OH (US); Jeffrey Michael Kalman, Cleveland Heights, OH (US); Mark Louis Vitantonio, South Russell, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 11/410,808

(22) Filed: Apr. 25, 2006

(65) Prior Publication Data

US 2006/0185105 A1 Aug. 24, 2006

Related U.S. Application Data

(63) Continuation of application No. 10/384,806, filed on Mar. 10, 2003, now abandoned.

(51) Int. Cl.
*A61C 17/22* (2006.01)
(52) U.S. Cl. .................... 15/22.1; 15/22.2; 15/22.4
(58) Field of Classification Search .......... 15/22.1, 15/22.2, 22.4, 28
See application file for complete search history.

(56) References Cited

U.S. PATENT DOCUMENTS

| | | | |
|---|---|---|---|
| 1,517,320 A * | 12/1924 | Stoddart | 15/22.1 |
| 1,557,244 A | 10/1925 | Dominque | |
| 2,140,307 A * | 12/1938 | Belaschk et al. | 15/28 |
| 2,215,031 A | 9/1940 | Elmore | |
| 3,129,449 A | 4/1964 | Cyzer | |
| 3,159,859 A | 12/1964 | Rasmussen | |
| 3,233,265 A | 2/1966 | Alfred et al. | |
| 3,240,077 A | 3/1966 | Smith | |
| 3,242,516 A | 3/1966 | Cantor | |
| 3,592,188 A | 7/1971 | Barnett | |
| 4,274,173 A | 6/1981 | Cohen | |
| 4,374,354 A | 2/1983 | Petrovic | |
| 4,766,630 A | 8/1988 | Hegemann | |
| 4,845,795 A | 7/1989 | Crawford et al. | |
| 4,989,287 A | 2/1991 | Scherer | |
| 5,020,179 A | 6/1991 | Scherer | |
| 5,033,150 A | 7/1991 | Gross et al. | |
| 5,035,020 A | 7/1991 | Winiewski | |

(Continued)

FOREIGN PATENT DOCUMENTS

| | | |
|---|---|---|
| CA | 1082408 | 7/1980 |
| CA | 1330383 | 6/1994 |
| CN | 2236827 Y | 10/1996 |
| CN | 2271352 Y | 12/1997 |
| CN | 2271353 Y | 12/1997 |

(Continued)

*Primary Examiner*—Mark Spisich
(74) *Attorney, Agent, or Firm*—Richard Alexander; Kathleen Carter; Vladimir Vitenberg

(57) ABSTRACT

An electric toothbrush is provided. The electric toothbrush has an elongated body including a handle, a head, and a neck extending between the handle and the head. A first bristle carrier having a plurality of bristles and a second bristle carrier having a plurality of bristles are disposed on the head and each of the first and second bristle carriers have an opening. An electric motor is operatively connected to a shaft, wherein operation of the electric motor moves the shaft in an orbital motion and wherein the shaft is operatively connected to the first and second bristle carriers to move the first and second bristle carriers.

11 Claims, 13 Drawing Sheets

U.S. PATENT DOCUMENTS

| | | | |
|---|---|---|---|
| 5,068,939 A | 12/1991 | Holland | |
| 5,070,567 A | 12/1991 | Holland | |
| 5,088,145 A | 2/1992 | Whitefield | |
| 5,120,225 A | 6/1992 | Amit | |
| 5,142,723 A | 9/1992 | Lustig et al. | |
| 5,170,525 A | 12/1992 | Cafaro | |
| 5,177,826 A | 1/1993 | Vrignaud et al. | |
| 5,186,627 A | 2/1993 | Amit | |
| 5,226,206 A | 7/1993 | Davidovitz et al. | |
| 5,253,382 A | 10/1993 | Beny | |
| 5,259,083 A | 11/1993 | Stansbury, Jr. | |
| 5,274,870 A | 1/1994 | Stollmen | |
| 5,276,932 A | 1/1994 | Byrd | |
| 5,321,866 A * | 6/1994 | Klupt | 15/22.1 |
| 5,353,460 A | 10/1994 | Bauman | |
| 5,359,747 A | 11/1994 | Amakasu | |
| 5,383,242 A | 1/1995 | Bigler et al. | |
| 5,416,942 A | 5/1995 | Baldacci et al. | |
| 5,435,032 A | 7/1995 | McDougall | |
| 5,435,034 A | 7/1995 | Bigler et al. | |
| 5,465,444 A | 11/1995 | Bigler et al. | |
| 5,481,775 A | 1/1996 | Gentile et al. | |
| 5,500,970 A | 3/1996 | Maurer et al. | |
| 5,504,958 A * | 4/1996 | Herzog | 15/22.1 |
| 5,504,959 A | 4/1996 | Yukawa et al. | |
| 5,524,312 A | 6/1996 | Tan et al. | |
| 5,528,786 A | 6/1996 | Porat et al. | |
| 5,577,285 A | 11/1996 | Drossler | |
| 5,617,601 A | 4/1997 | McDougall | |
| 5,617,603 A | 4/1997 | Mei | |
| 5,625,916 A | 5/1997 | McDougall | |
| 5,679,991 A | 10/1997 | Wolf | |
| 5,732,432 A | 3/1998 | Hui | |
| 5,732,433 A | 3/1998 | Gocking et al. | |
| 5,778,474 A * | 7/1998 | Shek | 15/22.1 |
| 5,784,743 A | 7/1998 | Shek | |
| 5,836,030 A | 11/1998 | Hazeu et al. | |
| 5,842,245 A * | 12/1998 | Pai | 15/22.1 |
| 5,850,655 A | 12/1998 | Gocking et al. | |
| 5,862,558 A | 1/1999 | Hilfinger et al. | |
| 5,867,856 A | 2/1999 | Herog | |
| 5,876,206 A | 3/1999 | Maurer | |
| 5,901,397 A | 5/1999 | Hafele et al. | |
| 5,974,613 A | 11/1999 | Herog | |
| 5,974,615 A | 11/1999 | Schwarz-Hartmann et al. | |
| 5,987,688 A * | 11/1999 | Roberts et al. | 15/167.1 |
| 5,996,157 A | 12/1999 | Smith et al. | |
| 6,000,083 A * | 12/1999 | Blaustein et al. | 15/28 |
| 6,021,538 A | 2/2000 | Kressner et al. | |
| 6,032,313 A | 3/2000 | Tsang | |
| 6,138,310 A | 10/2000 | Porper et al. | |
| 6,178,579 B1 | 1/2001 | Blaustein et al. | |
| 6,189,693 B1 | 2/2001 | Blaustein et al. | |
| 6,195,828 B1 | 3/2001 | Fitsch | |
| 6,209,164 B1 | 4/2001 | Sato | |
| 6,230,717 B1 | 5/2001 | Marx et al. | |
| 6,237,178 B1 | 5/2001 | Krammer et al. | |
| 6,308,358 B2 | 10/2001 | Gruber et al. | |
| 6,308,359 B2 | 10/2001 | Fritsch et al. | |
| 6,311,837 B1 | 11/2001 | Blaustein et al. | |
| 6,347,425 B1 | 2/2002 | Fattori | |
| 6,360,395 B2 | 3/2002 | Blaustein et al. | |
| 6,363,565 B1 | 4/2002 | Pathrath | |
| 6,408,473 B1 | 6/2002 | Kessler | |
| 6,446,294 B1 | 9/2002 | Specht | |
| 2001/0020314 A1 | 9/2001 | Calabrese | |
| 2002/0157197 A1 | 10/2002 | Hafemann | |
| 2003/0140436 A1* | 7/2003 | Gatzemeyer et al. | 15/22.1 |
| 2003/0182746 A1* | 10/2003 | Fattori et al. | 15/22.1 |

FOREIGN PATENT DOCUMENTS

| | | | |
|---|---|---|---|
| CN | 2274947 Y | 2/1998 | |
| CN | 2324988 | 6/1999 | |
| DE | 2736286 | 7/1978 | |
| DE | 8426426 | 3/1985 | |
| DE | 3406112 | 8/1985 | |
| DE | 3833358 | 4/1989 | |
| DE | 4313970 | * 11/1994 | |
| DE | 29618755 | * 3/1997 | |
| DE | 29517610 | 4/1997 | |
| DE | 19603851 | 8/1997 | |
| DE | 19701964 | 8/1998 | |
| DE | 29809977 | 2/1999 | |
| EP | 254397 | 1/1988 | |
| EP | 259648 | 3/1988 | |
| EP | 208401 | 5/1991 | |
| EP | 537465 | 4/1993 | |
| EP | 546203 | 6/1993 | |
| EP | 0628291 | 12/1994 | |
| EP | 546203 | 8/1996 | |
| EP | 0 758 857 B1 | 2/1997 | |
| EP | 1053721 | 11/2000 | |
| EP | 1093770 A | 4/2001 | |
| FR | 1250455 | 10/1959 | |
| FR | 2337524 | 8/1977 | |
| FR | 2616306 | 12/1988 | |
| GB | 1488628 | 12/1976 | |
| GB | 1583558 | 1/1981 | |
| GB | 2228861 | 9/1990 | |
| GB | 2247297 | * 2/1992 | |
| GB | 2290224 | 12/1995 | |
| GB | 2319170 | 5/1998 | |
| GB | 2359739 | 9/2001 | |
| JP | 57-89810 | 6/1982 | |
| JP | U4-133733 | 7/1991 | |
| JP | 05-146313 A | 6/1993 | |
| JP | 5-146314 | 6/1993 | |
| JP | 5-161509 | 6/1993 | |
| JP | 5-199917 | 8/1993 | |
| JP | 5-269023 | 10/1993 | |
| JP | 6-189822 | 7/1994 | |
| JP | 7-116024 | 5/1995 | |
| JP | 7-163420 | 6/1995 | |
| JP | 8-322641 | 10/1996 | |
| JP | 8-322641 | * 12/1996 | |
| JP | 9-140456 | * 6/1997 | |
| JP | 10-66704 | * 3/1998 | |
| JP | 2804940 | 7/1998 | |
| JP | 2811246 | 8/1998 | |
| JP | 10-211221 | 11/1998 | |
| KR | 1986-0001137 | 6/1986 | |
| KR | 183429 | 3/2000 | |
| TW | 135303 | 10/1976 | |
| TW | 154730 | 3/1979 | |
| TW | 248031 | 12/1982 | |
| TW | 137856 | 7/1990 | |
| TW | 212909 | 9/1993 | |
| TW | 239963 | 2/1995 | |
| TW | 239964 | 2/1995 | |
| TW | 311444 | 12/1996 | |
| TW | 330410 | 12/1996 | |
| TW | 406557 | 5/1998 | |
| WO | WO 94/03125 | 2/1994 | |
| WO | WO 94/28823 | 12/1994 | |
| WO | WO 96/31171 | 10/1996 | |
| WO | 99/12492 | * 3/1999 | |
| WO | WO 99/12492 | 3/1999 | |
| WO | WO 03/071979 A1 | 9/2003 | |

* cited by examiner

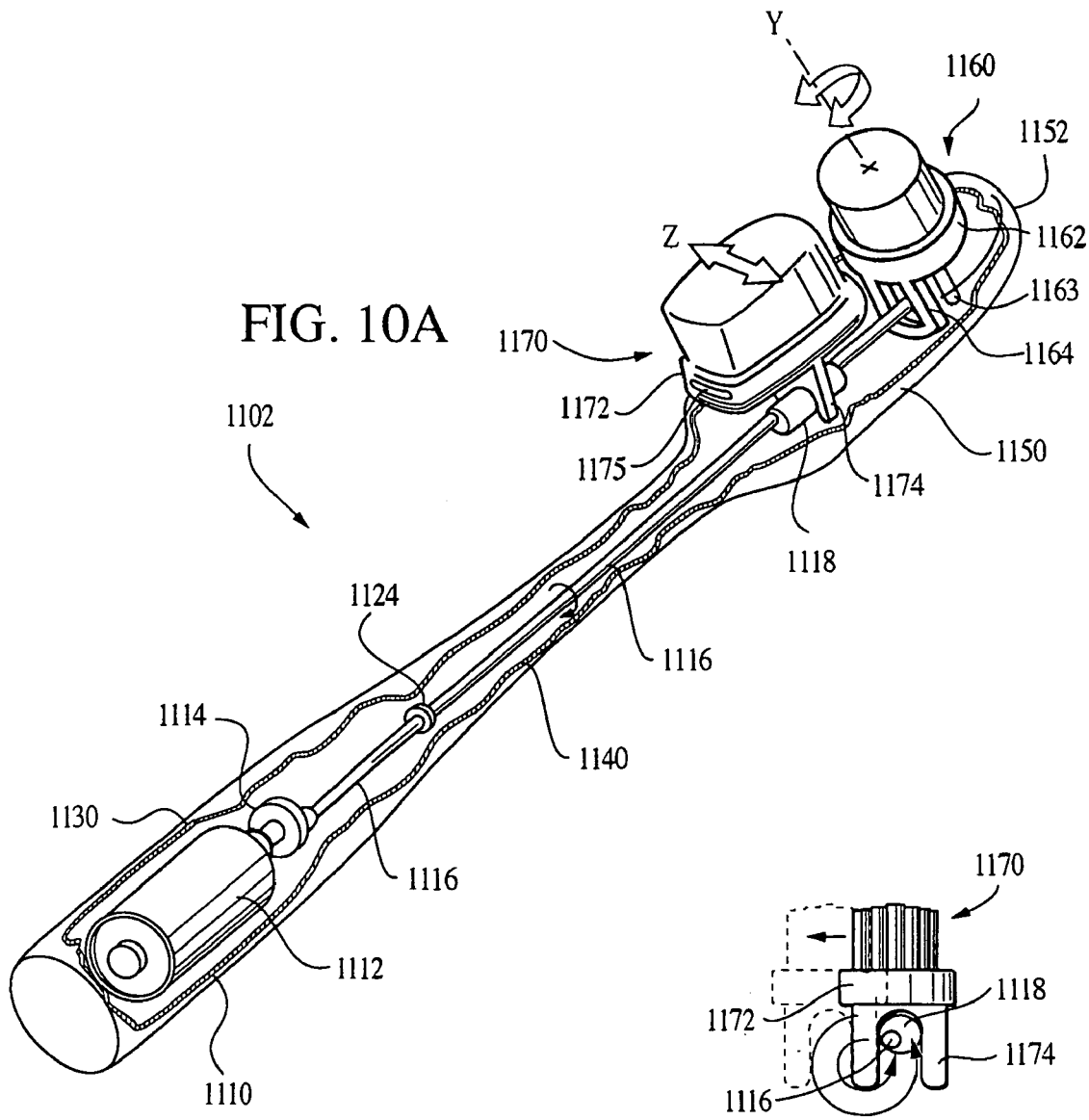
FIG. 10A
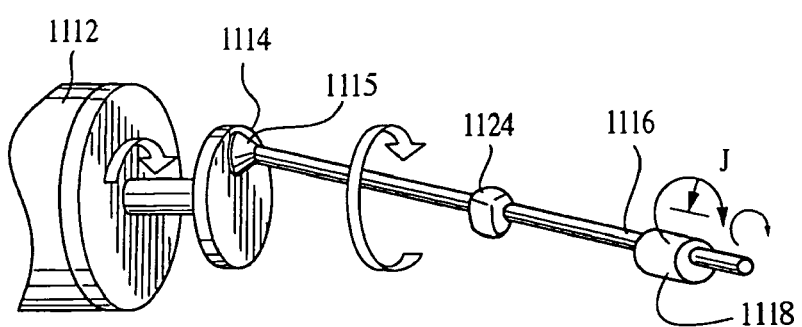
FIG. 10C
FIG. 10B

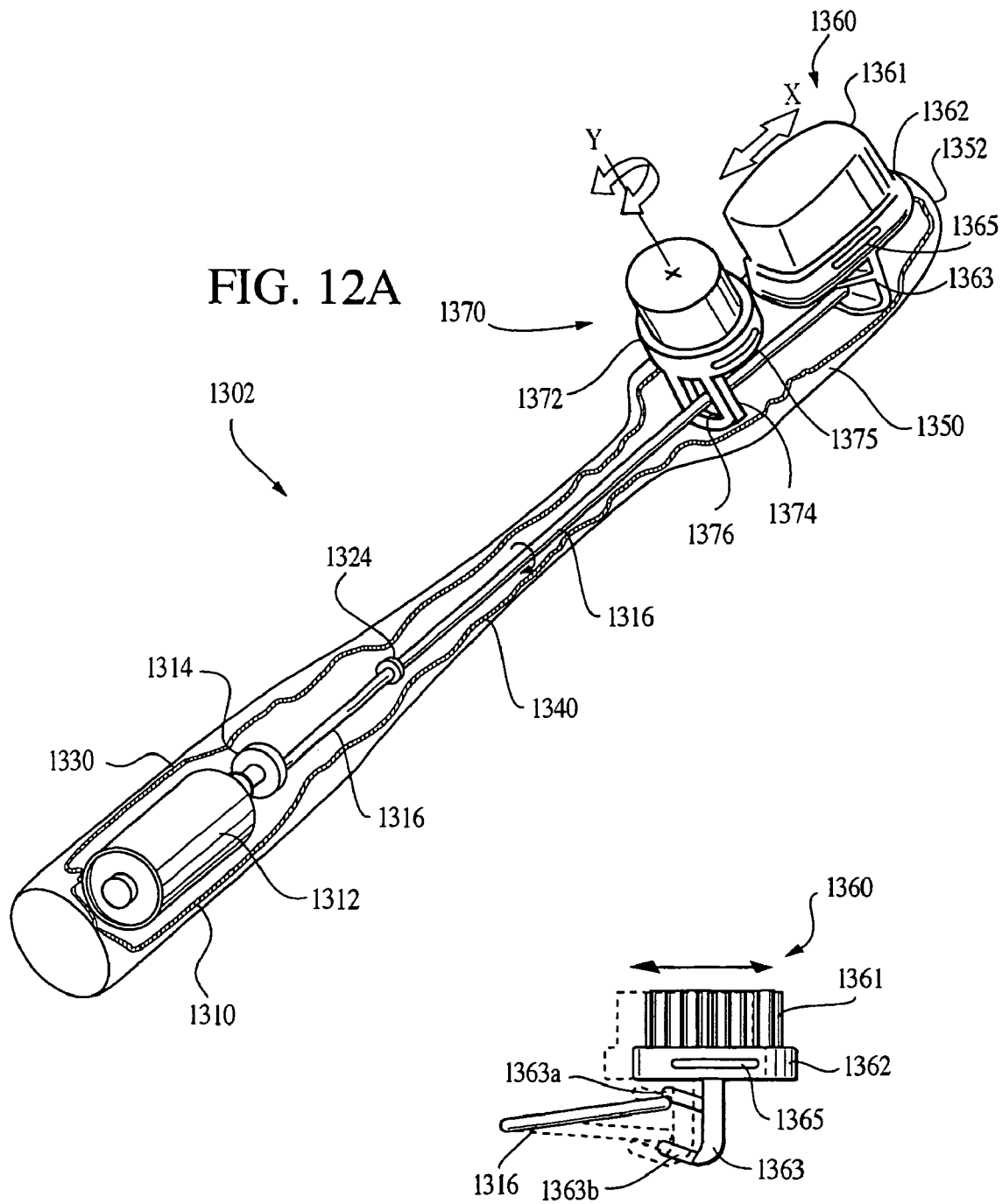

ELECTRIC TOOTHBRUSHES

CROSS REFERENCES TO RELATED APPLICATIONS

This is a continuation of application Ser. No. 10/384,806, filed Mar. 10, 2003, and now abandoned, the substance of which is incorporated by reference.

FIELD OF THE INVENTION

The present invention relates to the field of toothbrushes, and more particularly, the invention relates to the field of electrically powered toothbrushes.

BACKGROUND OF THE INVENTION

Most known electric toothbrushes utilize a single bristle carrier that is powered or otherwise driven by an electric motor incorporated in the toothbrush. The bristle carriers in these toothbrushes generally undergo rotary motion. Although satisfactory in certain respects, a need still exists for an improved powered toothbrush design.

Numerous attempts have been made to improve the design, efficiency, cleaning efficacy, simplicity, and/or commercial viability of electric toothbrushes. One approach has been the provision of multiple powered bristle carriers. Most artisans have grouped multiple sets of bristles along an end of a brush and incorporated a drive mechanism for simultaneously rotating each of the bristle sets, together. Exemplary designs include those disclosed in U.S. Pat. Nos. 3,242,516; 4,156,620; 4,845,795; 5,088,145; 5,020,179; 4,827,550; and 4,545,087.

A related strategy is to group sets of bristles on multiple rotating bristle carriers, as disclosed in U.S. Pat. Nos. 2,140,307 and 5,170,525. Rather than rotating each individual bristle set about its center, i.e. the approach adopted in the previously noted patents, the designs described in the '307 and '525 patents rotate multiple groups of bristle sets about the center of a bristle carrier. Specifically, multiple groups of bristle sets are disposed on a circular bristle carrier and that bristle carrier, typically one of several, is rotated about its own axis.

U.S. Pat. No. 5,070,567 describes a design combining the two previously noted strategies. A rotating bristle carrier is provided along with multiple individually rotatable bristle sets. Although this design likely provides many of the advantages associated with each of its predecessors, the cleaning efficacy of spinning bristle sets, alone, is somewhat limited.

Yet another design is disclosed in U.S. Pat. No. 5,617,603. The '603 patent describes an assembly of "staggered swing" brushes. Apparently, the two bristle carriers move along a complex path within the plane of the toothbrush.

Although dual bristle carriers that undergo various combinations of movement have been disclosed in the prior art, there remains a need to provide an electric toothbrush with a bristle carrier that undergoes a different type of motion. More significantly, there is a need to provide an electric toothbrush with multiple bristle carriers that provide additional types of motion and combinations of motion.

SUMMARY OF THE INVENTION

An electric toothbrush is provided. The electric toothbrush has an elongated body including a handle, a head, and a neck extending between the handle and the head. A first bristle carrier having a plurality of bristles and a second bristle carrier having a plurality of bristles are disposed on the head and each of the first and second bristle carriers have an opening. An electric motor is operatively connected to a shaft, wherein operation of the electric motor moves the shaft in an orbital motion and wherein the shaft is operatively connected to the first and second bristle carriers to move the first and second bristle carriers.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which:

FIG. 10A is a perspective view of another preferred embodiment toothbrush in accordance with the present invention, wherein portions of the body, neck and head have been removed for clarity.

FIG. 10B is a partial perspective view of a motor, drive assembly, drive shaft, and pivot member used in the toothbrush of FIG. 10A.

FIG. 10C is an elevational view of the bristle carrier and cam member used in the toothbrush of FIG. 10A illustrating the motion of the bristle carrier.

FIG. 12A is a perspective view of another preferred embodiment toothbrush in accordance with the present invention, wherein portions of the body, the neck, and the head of the toothbrush have been removed for clarity.

FIG. 12B is an elevational view of the bristle carrier of the toothbrush depicted in FIG. 12A.

DETAILED DESCRIPTION OF THE PREFERRED EMBODIMENTS

Before describing the various preferred embodiments, it is instructive to define the various types of motions that the movable bristles of the various toothbrushes may undergo. As used herein, the term "angular motion" refers to any angular displacement. "Linear motion" is movement along a straight or substantially straight, line or direction. "Curvilinear motion" is movement that is neither completely linear nor completely angular but is a combination of the two (e.g., curvilinear). These motions can be constant or periodic. Constant motion refers to motion that does not change direction or path (i.e., is unidirectional). Periodic motion refers to motion that reverses direction or path. Constant angular motion is referred to as rotary motion, although features herein may be described as "rotatably mounted" which is intended to merely mean that angular motion, whether periodic or constant, is possible. Periodic angular motion is referred to as oscillating motion. Curvilinear motions can also be either constant (i.e., unidirectional) or periodic (i.e., reverses direction). Periodic linear motion is referred to as "reciprocation". "Orbital motion" is a type of angular motion about an axis that is distinct from and is some distance apart from the center of the moving component, e.g. a shaft. This distance is referred to herein as the extent of offset of the orbital motion. Orbital motion may be either constant angular motion or periodic angular motion.

Figure 1A:
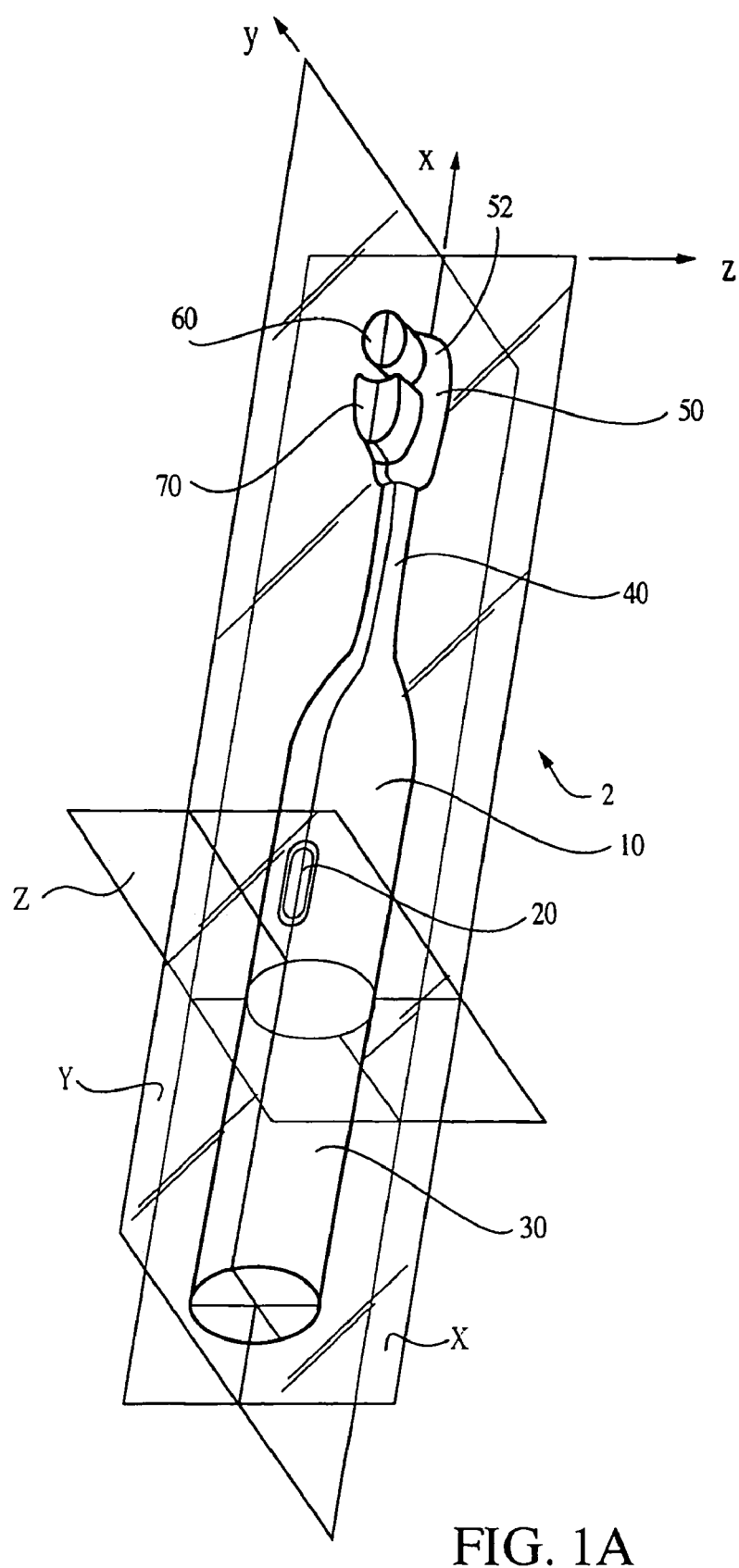
FIG. 1A is a perspective view of a preferred embodiment toothbrush in accordance with the present invention illustrating various planes and their orientation with respect to the toothbrush.

The above-described motions can occur along one or more axes of a bristle carrier, a toothbrush, a toothbrush head, etc. Accordingly, motion is described herein as being either one, two, or three dimensional motion depending upon the number of axial coordinates required to describe the position of a bristle carrier during its movement. The axes, X, Y, and Z, are shown in FIG. 1A. One dimensional motion is motion that can be described by a single coordinate (e.g., X, Y, or Z coordinates). Typically, only linear motion can be one dimensional. For example, periodic linear motion substantially along only the Y axis is one dimensional motion (referred to herein as a "pulsing motion" or an "up and down motion"). Two dimensional motion is movement by a bristle carrier that requires two coordinates (e.g., X and Y coordinates) to describe the path of travel of the bristle carrier. Angular motion that occurs in a single plane is two dimensional motion since a point on a bristle carrier would need two coordinates to describe the path of travel. Three dimensional motion is movement by a bristle carrier that requires three coordinates (e.g., X, Y, and Z coordinates) to describe the path of travel of the bristle carrier. An example of three dimensional motion is movement by a bristle carrier in the path of a helix.

Since most of the bristle carrier motions described herein can be modified by adjusting various structural features, the description of a motion herein shall be automatically understood to accommodate these variations. For example, a motion that is described as oscillating about an axis can also include components of other motions (e.g., a reciprocating linear motion), especially where it is noted that modifications can be made to provide this second component of motion. Motions that are intended to exclude such modifications shall be described herein with the modifier "primarily" (e.g., "primarily oscillating" or "primarily reciprocating") and are intended to exclude significant other types motion, but not other motions that might be incidental from manufacturing tolerances or variabilities or where it is difficult to completely eliminate another type of motion completely from the bristle carrier, as is sometimes the case. All motions described herein may be restricted to primarily the motion described if desired.

FIG. 1A is a perspective view of a preferred embodiment toothbrush 2 in accordance with the present invention. The toothbrush 2 comprises an elongated body 10 having a handle 30, a head 50, and a neck 40 extending between the handle 30 and the head 50. A switch 20 is provided or made accessible along the outer region of the body 10. As will be appreciated, the switch 20 actuates an electrical motor contained within the body 10 of toothbrush 2. The motor (not shown) and a drive mechanism as described herein (not shown) drive one or more bristle carriers disposed near a distal end of the toothbrush. Specifically, the toothbrush 2 further includes a first bristle carrier 60 located adjacent a distal-most first end 52 and a second bristle carrier 70. As described in greater detail herein, upon activation of the drive mechanism, the first and second bristle carriers undergo a particular combination of motions. The motions are best described in terms of the axes X, Y, and Z.

The X axis is generally referred to herein as the longitudinal axis and generally extends along a longitudinal or lengthwise dimension (as seen from the top planar view of the toothbrush) of the toothbrush head or the bristle carrier. For example, a longitudinal axis is an axis passing through the longest dimension of the toothbrush head. The Y axis is transverse, orthogonal or perpendicular to the X axis and generally bisects the toothbrush head into its left and right halves. The Z axis is transverse, orthogonal or perpendicular to the X and Y axes. It will be appreciated that axis orientations need not be exactly orthogonal or perpendicular to another axis and that some deviation from 90 degrees between the axes, particularly when these axes are used to describe a direction of motion. It should be understood that any axis orientation herein can be modified by the terms "generally" or "substantially" (e.g., "generally transverse" or "substantially transverse"). The word "substantially" implies some angular deviation, but not as much angular deviation from 90 degrees as the word "generally". No modifier indicates slight to no deviation from 90 degrees. Thus, a motion that is described as occurring along a first axis transverse to a second axis implies that the motion occurs at a 90 degree angle to the second axis with some slight deviation permitted (e.g., from manufacturing tolerances, etc.). If the motion is generally transverse or substantially transverse, a greater deviation from 90 degrees is contemplated. All the axes described herein can intersect another axis either generally or substantially transverse to said other axis.

Plane X contains the X axis and is generally referred to herein as the plane of the toothbrush or the plane of the toothbrush head. This plane generally extends along the longitudinal dimension of the toothbrush. The Y plane contains the Y axis and extends through the toothbrush and is perpendicular to the X plane. The Y plane either bisects the toothbrush or is parallel to a plane that does. The Z plane is perpendicular to both the X plane and the Y plane and contains the Z axis.

Furthermore, it is useful to address the terminology used in describing the preferred embodiment toothbrushes, bristle carriers, and the various drive mechanisms. As used herein, the term "forward" refers to the direction from the handle to the head while the term "rearward" refers to the direction from the head to the handle. A longitudinal direction is a direction that generally corresponds to a longitudinal or X axis but which may not lie in the same plane as the axis. For example, the longitudinal axes of a shaft and a bristle carrier may not extend in the same plane but generally extend in the same direction from a top planar view. Similarly, a neck and head that are angled with respect to each other may not have longitudinal axes that extend in the same plane, but do have axes that extend in the same general longitudinal direction from a top planar view. Many of the preferred embodiment electric toothbrushes typically have an elongated head with a longitudinal axis passing through the longest dimension thereof. This axis typically extends in the same general direction as the longitudinal axes of the toothbrush neck and/or shaft. This axis is generally referred to as the longitudinal axis of the toothbrush. By the phrase "same general direction," some angular deviation is contemplated between the axes.

Generally, the preferred embodiment toothbrushes according to the present invention comprise an elongated hollow body containing an electrically powered motor and drive mechanism that is used to drive one, two, three or more moveable bristle carriers. The elongated hollow body also includes an interior chamber or cavity for containing one or more batteries for powering the motor. And, one or more switches are provided along the outer region of the body for activating the motor and drive mechanism. As will be appreciated, a removable end cap is provided to enclose the interior chamber and provide a seal against external agents for the components inside the toothbrush body. As described in detail herein, the preferred embodiment toothbrushes comprise one, two, three or more movable bristle carriers. Each of the bristle carriers undergoes particular types of motion and the resulting combinations of movements provide unique cleaning efficacy.

Furthermore, it is useful to define the terms "fixed" or "static" bristles, and the term "movable" bristles. The terms fixed or static bristles refer to bristles that are secured or affixed to the brush head or body of the toothbrush or other component thereof so that the bristles, and specifically, the base of the bristles, do not move with regard to the longitudinal axis of the toothbrush. Restated, fixed or static bristles refer to bristles that are affixed to the toothbrush such that their base or point of attachment does not move with respect to the toothbrush. It is recognized that the tips or regions distal from the base of a bristle or group of bristles may move as a result of flexing of the bristle. However, the base of a stationary, static, or fixed bristle does not move with respect to the brush. The term movable bristle refers to a bristle in which the base of the bristle moves with respect to the toothbrush, and particularly with respect to the longitudinal axis of the brush. Generally, this configuration is accomplished by affixing or supporting the base of the bristle to a mounting component, i.e. a bristle carrier or holder, that is movable with respect to the brush. Restated, a movable bristle is a bristle that is movable with respect to the longitudinal axis of the brush.

Figure 1B:
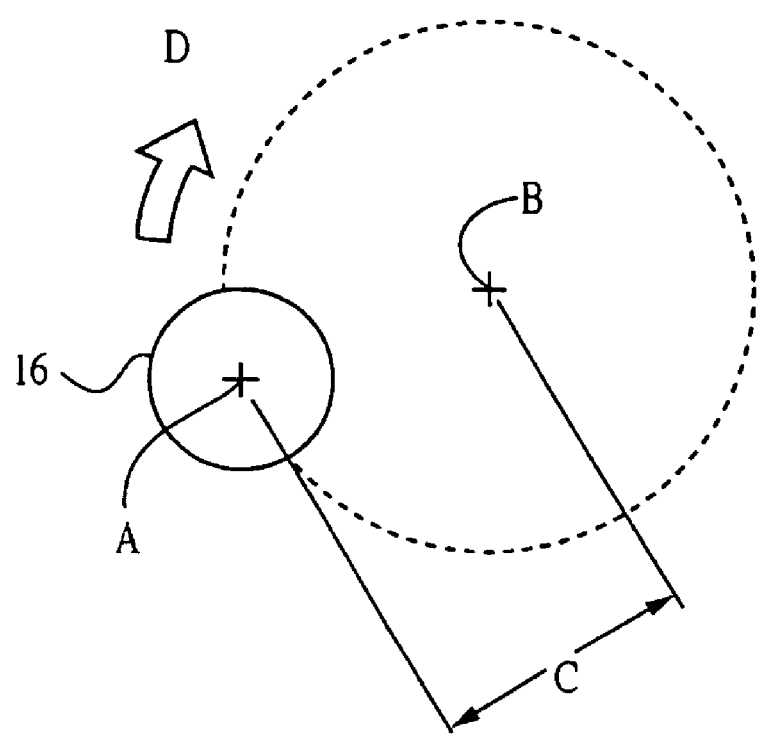
FIG. 1B is a schematic representation of a shaft undergoing orbital motion.
Figure 1C:
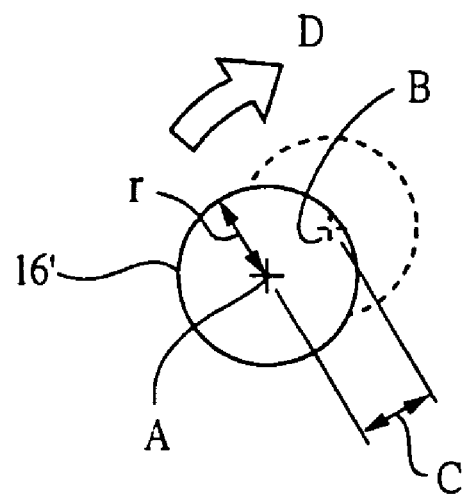
FIG. 1C is a schematic representation of another shaft undergoing orbital motion.

FIGS. 1B and 1C are schematic representations of a body undergoing orbital motion. Specifically, FIG. 1B depicts a drive shaft 16 shown in cross section and having a center A, being rotated in the direction of arrow D about an axis of rotation B. The degree of offset of the orbital motion is shown as distance C. Orbital motion may also be imparted upon a component in which the axis of rotation intersects or extends within the body itself. For instance, in FIG. 1C, drive shaft 16' having a center A is rotated in the direction of arrow D about an axis of rotation B. The degree of offset of the orbital motion is shown as distance C. In the orbital motion of FIG. 1C, the degree of offset C is less than the cross-sectional radius of the drive shaft, shown as r in FIG. 1C. Restated, the axis of rotation B extends within a portion of the drive shaft 16' rather than outside of the shaft 16'.

Various features are embodied in the present invention toothbrushes. Many of the preferred embodiment toothbrushes utilize a drive shaft that undergoes orbital motion upon activation of the toothbrush. While an orbital motion is preferred for the drive shaft, it will be appreciated that a shaft that rotates about its center can be substituted if the shaft is provided with a cam, such as described in U.S. application Ser. No. 09/993,167, filed Nov. 6, 2001. Various rotating drive shaft arrangements that would be suitable with such an arrangement are described in U.S. Pat. Nos. 6,178,579; 6,189, 693; 6,360,395; and 6,371,294.

Figure 2A:
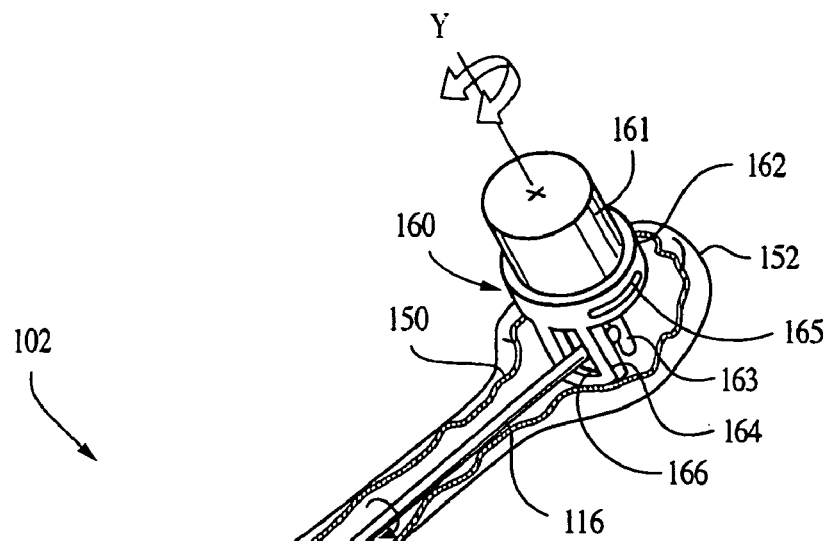
FIG. 2A is a perspective view of a preferred embodiment toothbrush in accordance with the present invention, wherein portions of the body, neck and head of the toothbrush has been removed for clarity.

FIG. 2A is a perspective view of a preferred embodiment toothbrush 102 in accordance with the present invention. Toothbrush 102 comprises a body 110, a switch (not shown), a handle 130, a head 150, and a neck 140 extending between the handle 130 and the head 150. Disposed within the body 110 is an electric motor 112 and an orbital motion assembly 114 operatively connected to a drive shaft 116 in a configuration, such as that shown in FIG. 2B. As described in greater detail herein, the drive shaft 116 preferably undergoes orbital motion and extends through, and is preferably supported and retained by a pivot member arrangement 124 defined within the interior of the neck 140 or body 110. In the toothbrush 102, the pivot member arrangement is a ball that is rotatably mounted within a socket (not illustrated), which is stationary. The drive shaft 116 extends through the ball to a movable bristle carrier disposed at the head 150 of the toothbrush 102. The ball and socket serve as a pivoting member. The shaft (which is preferably straight) does not undergo orbital motion at the ball and socket, as shown schematically in FIG. 2B. Other arrangements and configurations can be used in place of the ball and socket arrangement to provide a pivoting member. For example, the straight drive shaft 116 might pass through a stationary elastomeric sleeve that acts as a pivot member.

Referring further to FIG. 2A, a bristle carrier 160 is preferably disposed at a distal-most end 152 of the head 150. The bristle carrier 160 is a movable bristle carrier and is operatively connected to the drive shaft 116. The bristle carrier 160 has a plurality of bristles 161 grouped or arranged into tufts. The tufts of bristles can be secured to the head using techniques know in the art, such as stapling. Since the bristle carrier 160 is movable, the bristles 161 may be referred to as "movable bristles". The bristle carrier 160 includes a base 162 and an extension or collar 164 that defines an engagement slot or aperture 166. The collar 164 is preferably located at the rearward-most end of the bristle carrier 160. The collar 164 extends from the underside of the base 162 within the interior of the head 150 such that the distal end of the drive shaft 116 extends through the engagement slot or aperture 166. The bristle carrier 160 further includes a pin 163 that extends along a Y axis and is preferably co-linear with the center of the bristle carrier 160.

Upon the drive shaft 116 undergoing orbital motion, motion is imparted to the bristle carrier 160 by engagement between an outside portion of the shaft and one or more sides of the aperture. Depending upon the configuration of the aperture 166 and other factors, the motion of the bristle carrier 160 may be linear, angular, curvilinear, or combinations thereof. Since the bristle carrier 160 is rotatably mounted on the pin 163 extending from the center of the bristle carrier 160, the bristle carrier 160 primarily oscillates about a Y axis transverse to the longitudinal axis (e.g., X axis) of the toothbrush 102 and/or a longitudinal axis of the toothbrush head. The base 162 may optionally define one or more radially directed slots 165 that engage one or more fixed or stationary radially directed pins (not shown) that are embedded in or otherwise formed in the head 150 to further guide the motion of the bristle carrier 160 in a primarily oscillating movement.

Figure 2C:
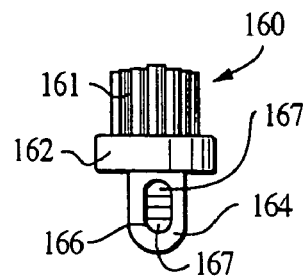
FIG. 2C is an elevational view of a bristle carrier of the preferred embodiment toothbrush depicted in FIG. 2A.
Figure 2B:
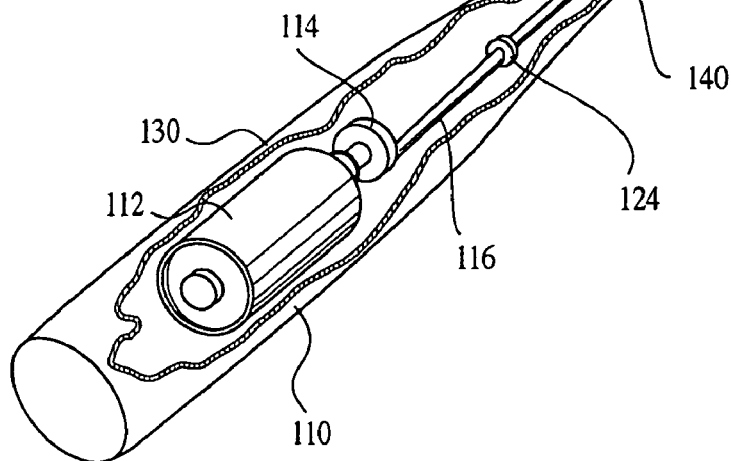
FIG. 2B is a partial perspective view of a motor, drive assembly, drive shaft, and pivot member used in the toothbrush depicted in FIG. 2A.
Figure 2B:
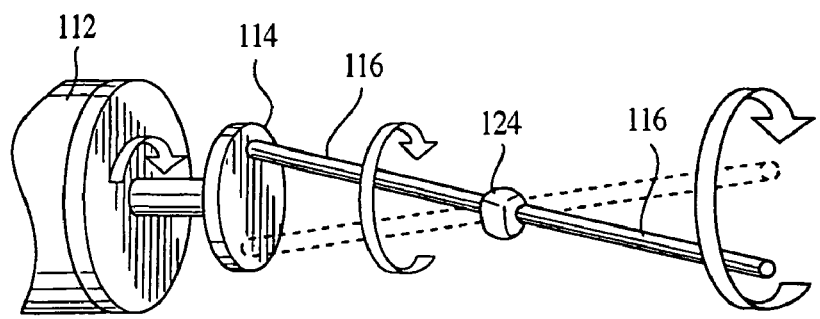

FIG. 2C is an end view of the bristle carrier 160 of the toothbrush 102 shown in FIG. 2A. The carrier 160 includes a plurality of bristles 161 (grouped into tufts) extending upward from the base 162. As can be seen, the base 162 includes the collar 164 that defines the engagement slot or aperture 166 through which the drive shaft 116 preferably extends. Most preferably, effective amounts of a dampening material 167 are disposed within the engagement slot or aperture 166 to reduce or minimize linear movement of the bristle carrier 160 along the Y axis of oscillation that otherwise would result when the shaft 116 impacts the top and bottom portions of the aperture 166. This dampening material can also assist in reducing noise during operation. Alternatively, the length of the aperture 166 can be increased so that the shaft 116 does not impact the top and bottom portions of the aperture during its orbital motion. Similarly, the bottom portion of the collar 164 can be removed (see, e.g., FIG. 3) so that the shaft 116 does not impact a bottom portion of the aperture. The dampening material may be formed from any resilient material that can absorb the repeated impacts from the shaft 116, such as a thermoplastic elastomer or rubber. The movement of the bristle holder 160 can be governed by the shape and size of the aperture 166 as well as the location of the collar 164 along the bristle carrier 160 and/or the amount and nature of the dampening material. For example, as the width of the aperture 166 increases, the amplitude of the oscillating movement may decrease. If the dampening material is removed, the bristle carrier 160 may also reciprocatingly move in a direction along the Y axis in addition to oscillating about the axis of the pin 163. The combination of these motions would produce a complex motion.

Figure 3:
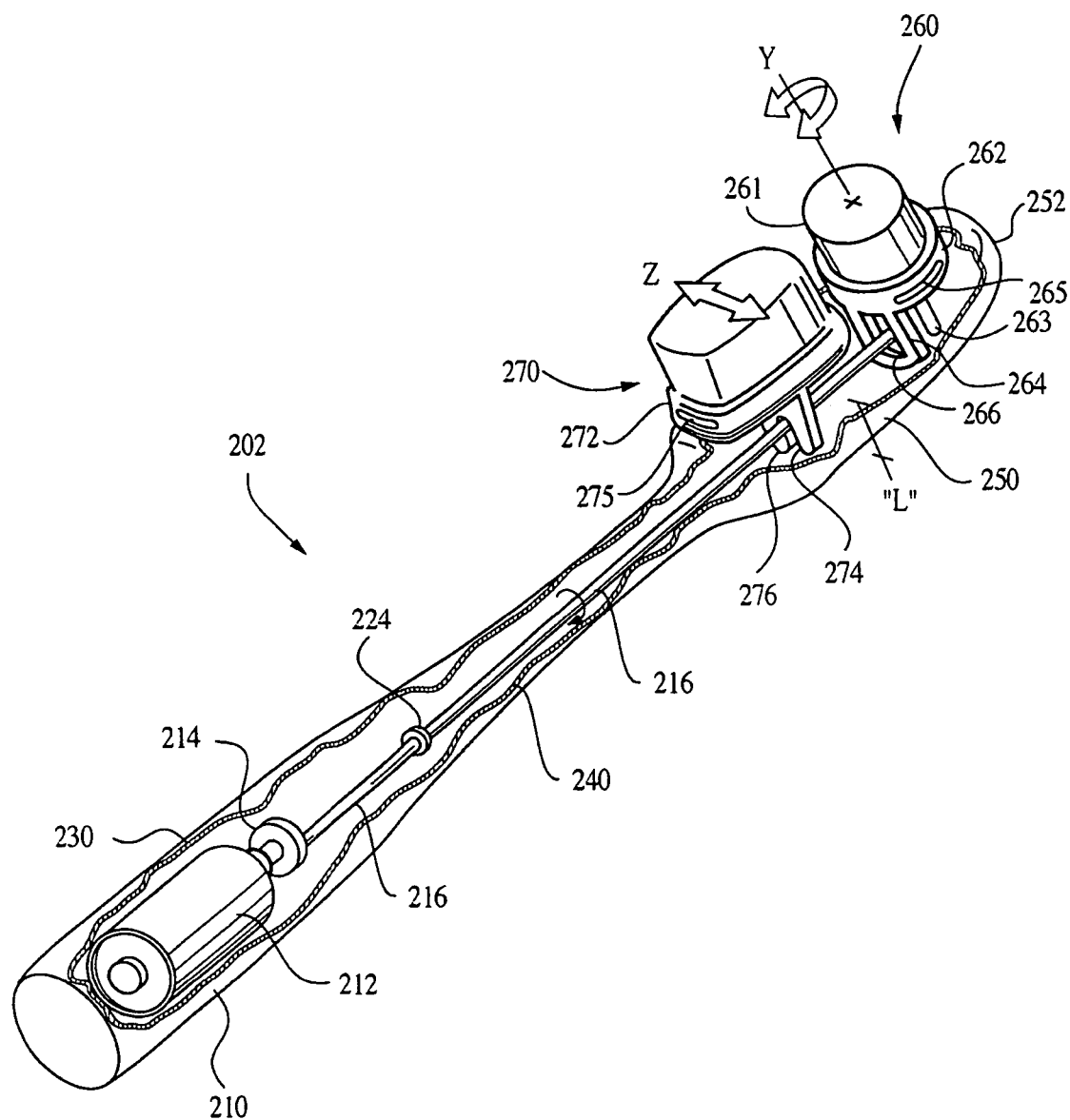
FIG. 3 is a perspective view of another preferred embodiment toothbrush in accordance with the present invention, wherein portions of the body, neck and head of the toothbrush have been removed for clarity.

FIG. 3 illustrates a perspective view of another preferred embodiment toothbrush 202 having a plurality of bristle carriers in accordance with the present invention. The toothbrush 202 comprises a body 210 having a switch (not shown), a handle 230, a head 250, and a neck 240 extending between the handle 230 and the head 250. Disposed within the interior region of the body 210 is an electric motor 212, an orbital motion assembly 214, and a drive shaft 216. The assembly 214 comprises a disk that is operatively coupled to the electric motor so that the disk rotates about the central axis of the motor. Gearing (not shown) may be provided between the disk and the motor to vary the rotational speed of the disk. The shaft 216 is eccentrically coupled to the disk so that the shaft undergoes an orbital motion when the motor is operating. A pivot member 224 is provided. Other arrangements can be used in place of the ball and socket arrangement to provide a pivoting member, as previously discussed. The drive shaft 216 preferably undergoes orbital motion. The collection of bristle carriers includes a first bristle carrier 260 disposed at a distal-most end 252 and a second bristle carrier 270 disposed between the first bristle carrier and the handle. The first bristle carrier 260 can be arranged and configured as previously described with respect to FIGS. 2A and 2C. The first bristle carrier 260 includes a plurality of bristles 261 extending from a base 262 having a collar 264 similar to the collar 164 shown in FIGS. 2A and 2C. The first bristle carrier 260 also preferably includes one or more radially directed slots 265 and a pin 263. The second bristle carrier 270 includes a base 272 also provided with a collar 274 located at the center of the second bristle carrier 270. The second bristle carrier 270 preferably has one or more slots 275 that engage one more longitudinally directed stationary or fixed pins (not shown) that are embedded in the head 250. The slots 275 and pins cooperate to guide the second bristle carrier 270 in a primarily reciprocating side-to-side motion transverse to the longitudinal axis of the toothbrush and/or head. Each of the collars defines an engagement slot or aperture 266 and 276 as previously described. Upon operation of the toothbrush 202 and orbital motion of the drive shaft 216, an outer portion of the shaft operatively engages each of the apertures of the first and second bristle carriers to impart motion thereto. In the embodiment depicted in FIG. 3, the first bristle carrier 260 can undergo the same motion as bristle carrier 160 of FIG. 2A, and the second bristle carrier 270 undergoes primarily reciprocating motion along a Z axis of the toothbrush 202 that is transverse to the longitudinal axis (e.g., X axis) of the toothbrush 202 and/or the head of the toothbrush. Depending on the shape and size of the aperture 276 of the second bristle carrier 270, the motion of the second bristle carrier 270 can be varied. For example, as the length L of the aperture 276 decreases, some movement in a Y axis direction may be imparted to the second bristle carrier 270, although the method of mounting the second bristle carrier 270 to the head of the toothbrush may have to modified to accommodate this motion, such as by increasing the size of the slots 275 to accommodate this motion.

Figure 4A:
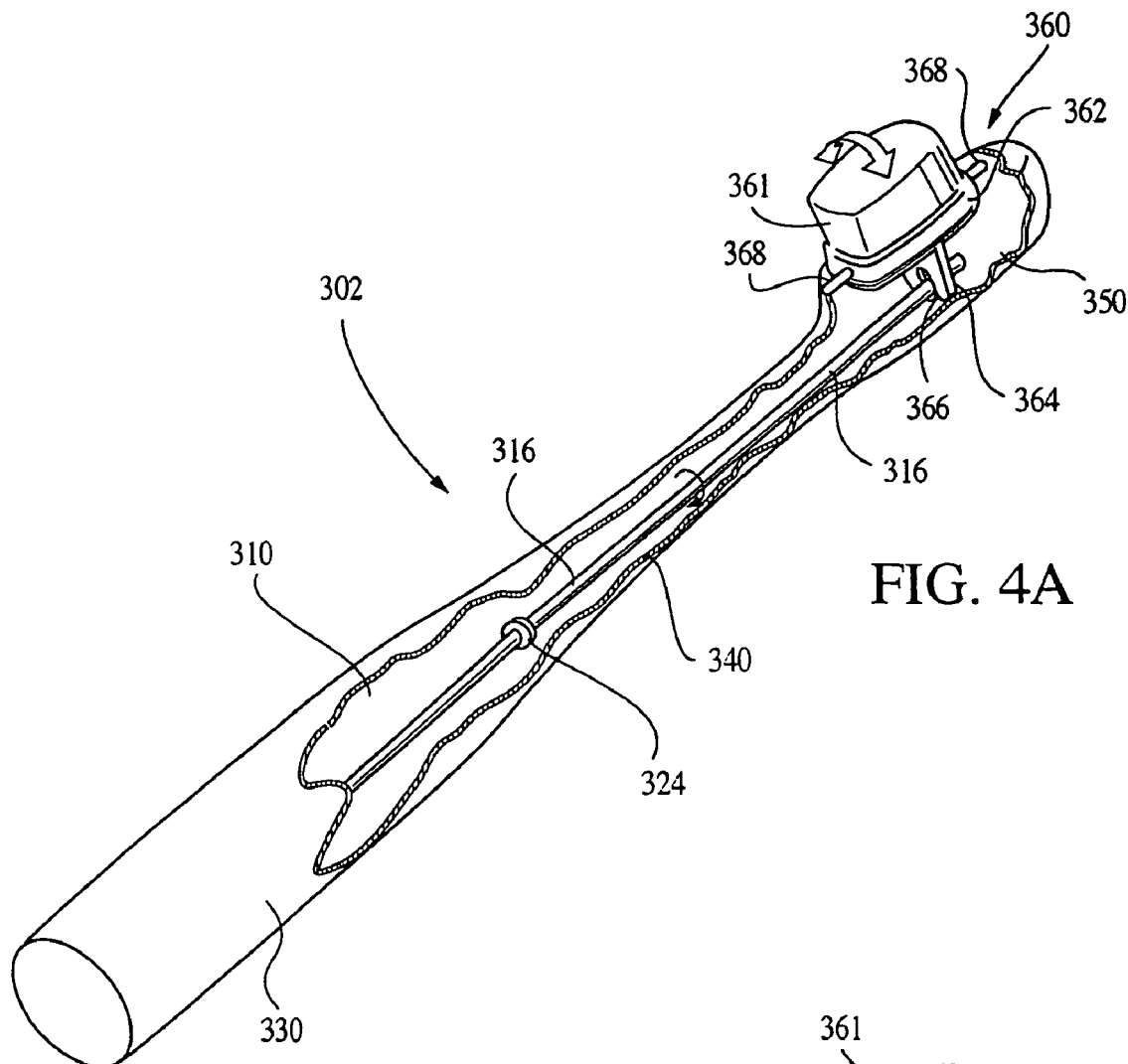
FIG. 4A is a perspective view of another preferred embodiment toothbrush in accordance with the present invention, wherein portions of the body, neck and head of the toothbrush have been removed for clarity.
Figure 4B:
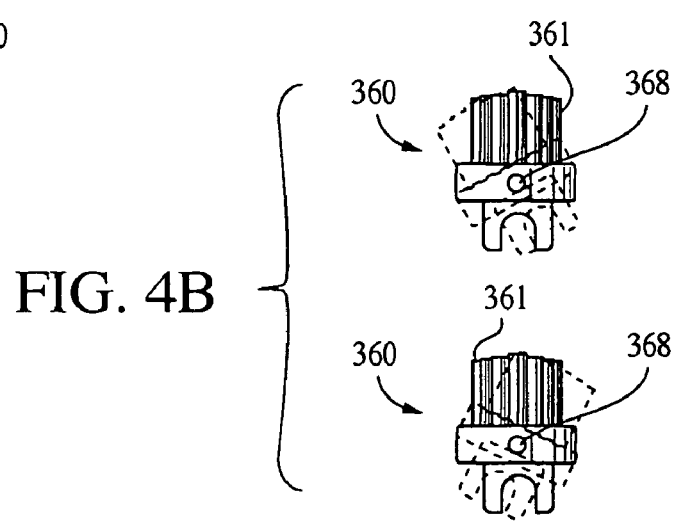
FIG. 4B is an elevational view of the bristle carrier used in the toothbrush of FIG. 4A illustrating the motion of the bristle carrier.

FIG. 4A is a perspective view of another preferred embodiment toothbrush 302 in accordance with the present invention. The toothbrush 302 comprises a body 310 having a handle 330, a head 350 and a neck 340 extending between the handle 330 and the head 350. The toothbrush 302 further includes a drive shaft 316 extending through a pivot member 324 to the brush head 350. The drive shaft 316 preferably undergoes orbital motion, the same as previously described. Disposed on the brush head 350 is a bristle carrier 360 having a plurality of bristles 361 extending from a base 362 with a collar 364 that defines an engagement slot or aperture 366. As can be seen, a distal end portion of the drive shaft 316 extends through the engagement slot or aperture 366. The collar 364 and the engagement slot are located at or near the center of the bristle carrier 360. The bristle carrier 360 is preferably elongate in shape, and, more preferably, is rectangular in top plan view. The base 362 may further be provided with one or more pivot members in the form of pins 368 that are retained or are otherwise engaged with corresponding holes in the brush head 350. The one or more pivot members 368 are provided to further govern or define the movement of the bristle carrier 360. In the embodiment shown in FIG. 4A, the bristle carrier 360 oscillates about an axis extending through the pivot members 368 which extends in the same general direction as the longitudinal axis of the toothbrush 302. This oscillation occurs upon operation of the toothbrush 302 and orbital motion of the drive shaft 316, as best seen in FIG. 4B. The aperture 366 should have a length sufficient to avoid impact between the shaft 316 and the top and bottom portions of the aperture 366. As will be appreciated, the head 350 can include additional bristle carriers. For example, a bristle carrier similar to one of those of FIG. 3 can be provided in combination with the bristle carrier 360. These bristle carriers can be arranged in any order. For instance, the bristle carrier 260 of FIG. 3 might be located at the distal-most end and the bristle carrier 360 could be located between the bristle carrier 260 and the handle. Alternatively, the bristle carrier 270 of FIG. 3 could be combined with the bristle carrier 360, in any order or arrangement.

Figure 5A:
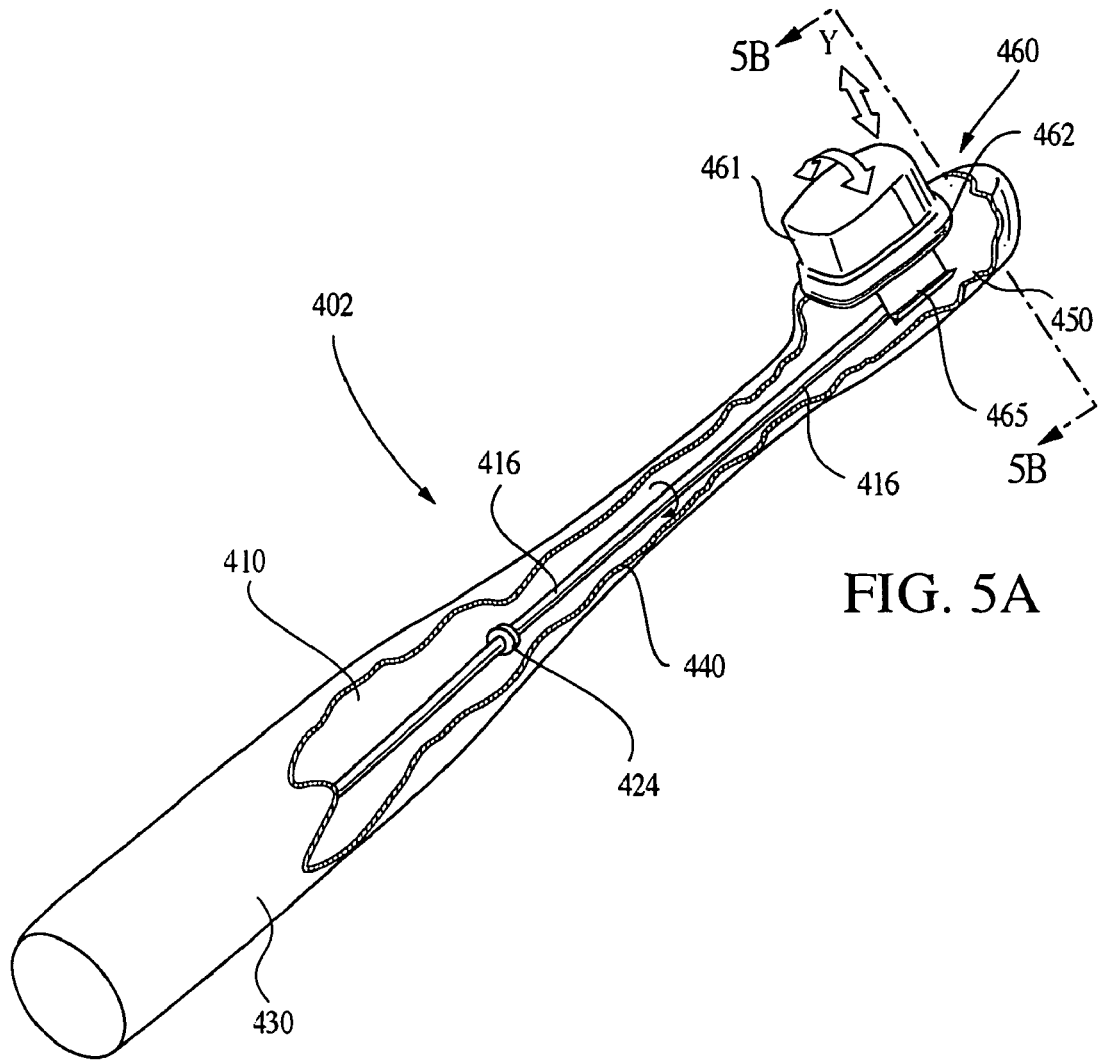
FIG. 5A is a perspective view of yet another preferred embodiment toothbrush in accordance with the present invention, wherein portions of the body, neck and head of the toothbrush have been removed for clarity.

FIG. 5A is a perspective view of another preferred embodiment toothbrush 402 in accordance with the present invention. The preferred embodiment toothbrush 402 includes a body 410 having a handle 430, a head 450 and a neck 440 extending between the handle 430 and the head 450. The toothbrush 402 further includes a drive shaft 416 extending within the body 410 and preferably through a pivot member 424. The drive shaft 416 preferably undergoes orbital motion. The toothbrush 402 also includes a bristle carrier 460 having a plurality of bristles 461 extending from a base 462. The drive shaft 416 extends through the neck 440 and into the head 450 of the toothbrush 402 such that the drive shaft 416 may periodically engage or otherwise contact the base 462 of the carrier 460. This relationship is illustrated in greater detail in FIG. 5B. The bristle carrier is loosely retained in the head 450 by one or more L-shaped extensions 465. The extensions permit the bristle carrier 460 to move in the Y and Z directions while still retained by the head 450.

Figure 5B:
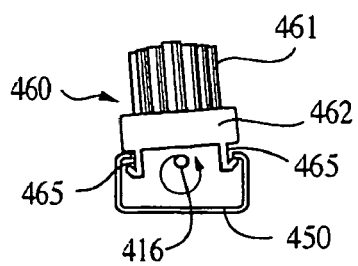
FIG. 5B is an elevational view of the bristle carrier of the preferred embodiment toothbrush depicted in FIG. 5A.

FIG. 5B is an end view of the bristle carrier 460 of the preferred embodiment toothbrush 402. As can be seen in FIG. 5B, as the drive shaft 416 undergoes orbital motion, the drive shaft 416 periodically contacts or otherwise engages the underside of the base 462 of the bristle carrier 460. Such engagement imparts a motion to the bristle carrier 460 that includes components of pulsing or reciprocating movement in the Y axis direction and a curvilinear oscillating movement generally about the longitudinal axis of the toothbrush and/or toothbrush head. Any of the bristle carriers of the previously described embodiments can also be combined with the bristle carrier 460 to provide a toothbrush with a plurality of moving bristle carriers.

Figure 6A:
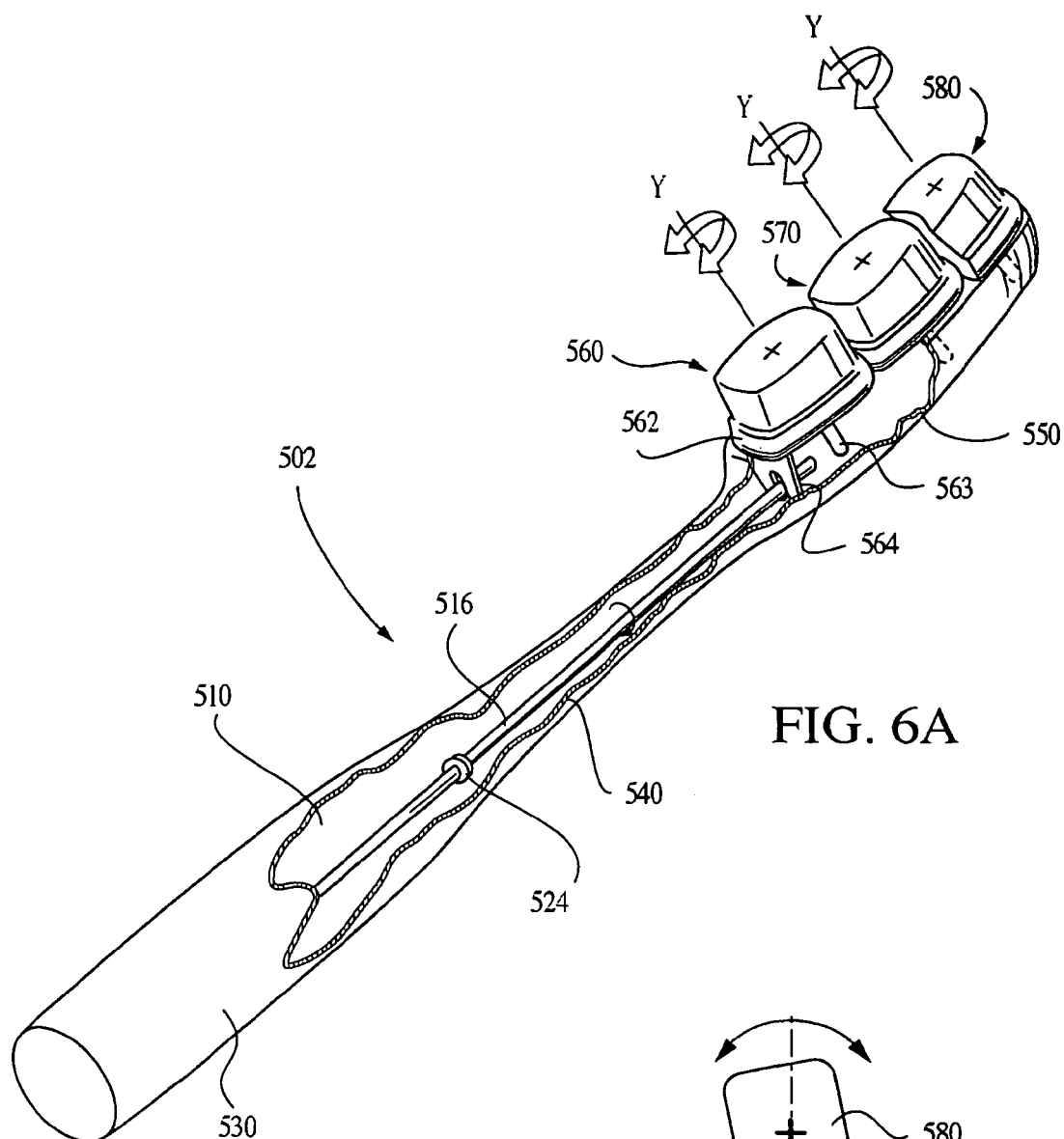
FIG. 6A is a perspective view of a preferred embodiment toothbrush in accordance with the present invention, wherein portions of the body, neck and head of the toothbrush have been removed for clarity.

FIG. 6A is a perspective view of a preferred embodiment toothbrush 502 in accordance with the present invention. The toothbrush 502 comprises a body 510 having a handle 530, a head 550, and a neck 540 extending between the handle 530 and the head 550. The toothbrush 502 further includes a drive shaft 516 extending within its interior and preferably through a pivot member arrangement 524. The drive shaft 516 preferably undergoes orbital motion. The drive shaft extends through a collar 564 of a first bristle carrier 560 disposed on the brush head 550. The first bristle carrier 560 includes a base 562, a collar 564, and a pin 563 as previously described herein. The collar is located near the rearward-most portion of the bristle carrier 560. The first bristle carrier 560 is rotatably disposed on the pin 563 such that the orbital motion of the drive shaft 516 causes the first bristle carrier 560 to oscillate about a Y axis that is transverse to the longitudinal axis of the toothbrush and/or head.

Figure 6B:
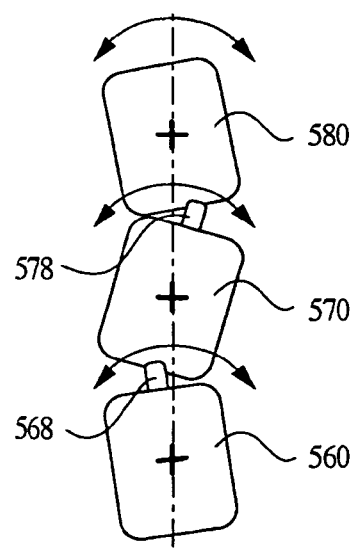
FIG. 6B is a top planar view of the plurality of bristle carriers of the toothbrush of FIG. 6A, illustrating their respective motions.

A second bristle carrier 570 is located adjacent the first bristle carrier 560 and a third bristle carrier 580 is located adjacent the second bristle carrier 570 such that the second bristle carrier is disposed between the first and third bristle carriers. FIG. 6B depicts the motion of the first bristle carrier 560, the second bristle carrier 570, and the third bristle carrier 580. Each of the second and third bristle carriers is operatively connected to its adjacent bristle carrier(s) rather than to the drive shaft 516. At least one of the bristle carriers e.g., 560 is operatively connected to the drive shaft 516. While only one bristle carrier is shown as operatively connect to the drive shaft, it will be appreciated that more than one bristle carrier can be so connected.

One or more pivot members or pins 568, 578 are disposed at one or more ends of each bristle carrier and are used to transmit motion from one bristle carrier to an adjacent bristle carrier. Thus, upon movement of one bristle carrier, such as bristle carrier 560, movement is imparted to an adjacent carrier, such as bristle carrier 570. And, upon movement of bristle carrier 570, movement is imparted to the bristle carrier 580. In this configuration, only one of the carriers need be directly powered from the drive shaft 516. That is, it is only necessary that one of the carriers 560, 570, or 580 be directly powered such as from the drive shaft 516. Each of the bristle carriers 570 and 580 is preferably mounted upon pins such as pin 563 of the first bristle carrier 560 and aligned in a Y axis direction so that the bristle carriers can oscillate about a Y axis generally transverse to the longitudinal axis of the toothbrush and/or the head, as shown in FIGS. 6A and 6B.

Figure 7:
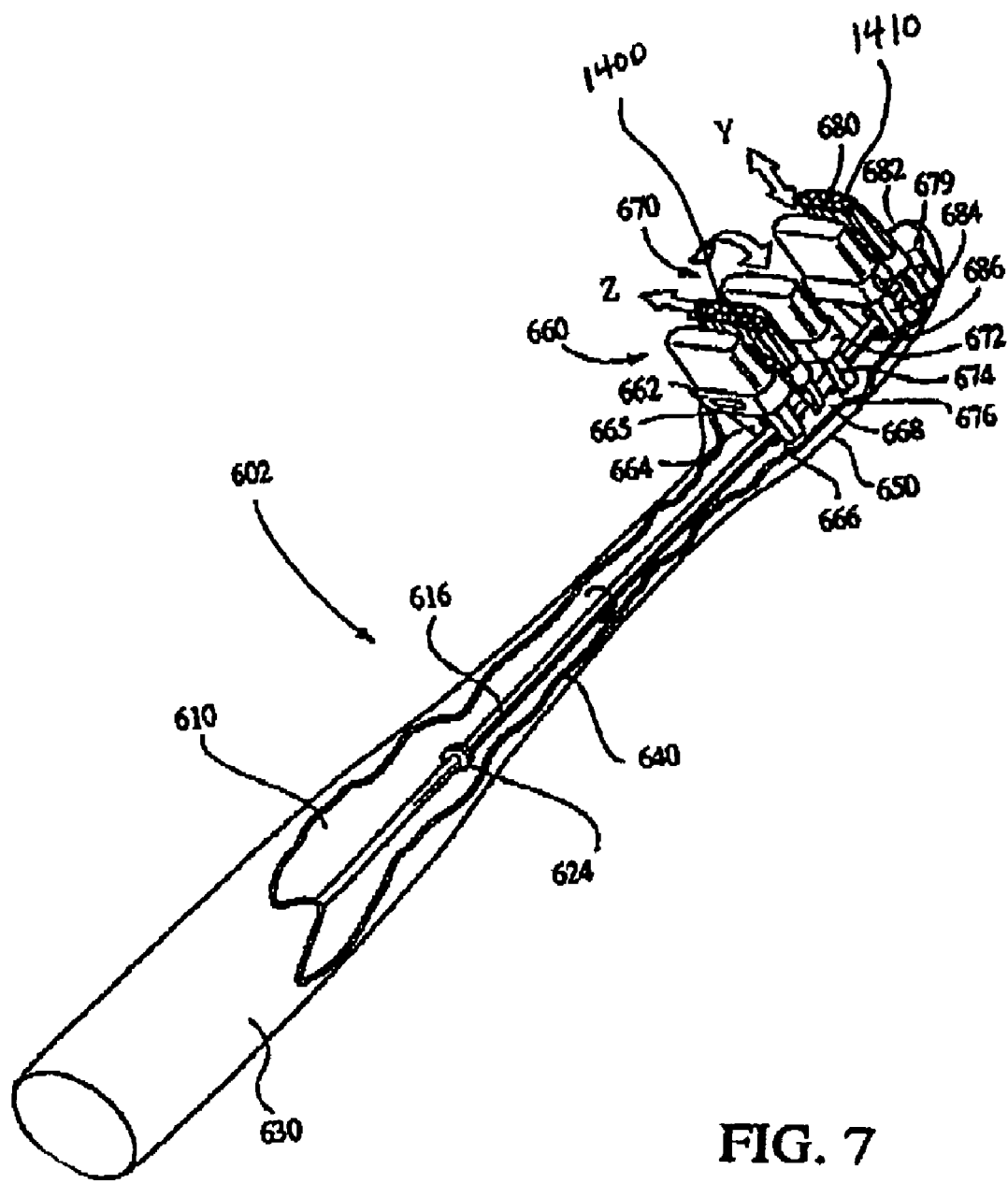
FIG. 7 is a perspective view of another preferred embodiment toothbrush in accordance with the present invention, wherein portions of the body, neck and head of the toothbrush have been removed for clarity.

FIG. 7 illustrates a perspective view of another preferred embodiment electric toothbrush 602 in accordance with the present invention. The preferred embodiment toothbrush 602 includes a body 610 having a handle 630 with a head 650 and a neck 640 extending between the handle 630 and the head 650. Extending within the interior of the body 610 is a drive shaft 616 that also preferably extends through a pivot member 624, as previously described. The drive shaft 616 preferably undergoes orbital motion. The distal end of the drive shaft 616 extends through a plurality or collection of collars described in greater detail herein. Disposed on the brush head 650 is a first bristle carrier 660 slidably mounted to the head, a second bristle carrier 670 rotatable mounted to the head, and a third bristle carrier 680 slidably mounted to the head. The first bristle carrier 660 has a base 662 with a collar 664 and one or more elongate slots 665 that cooperate with pins (not shown) in the head to guide the bristle carrier 660 in a side-to-side motion. The collar 664 defines an engagement slot or aperture 666. The second bristle carrier 670 includes a base 672, a collar 674 and one or more pivot members 668 in the form of longitudinally aligned pins which engage holes (not shown) in the head to guide the second bristle carrier in an oscillating movement. The collar 674 defines an engagement slot or aperture 676. The third bristle carrier 680 includes a base 682 and a collar 684. The collar 684 defines an engagement slot or aperture 686 that operatively engages the drive shaft 616 to impart motion to the bristle carrier 680. One or more elongate slots 679 are disposed on the sides of the bristle carrier 680 that engage pins (not shown) in the head. The elongate dimension of the slot 679 is aligned in the same general direction as a Y axis of the third bristle carrier to guide the third bristle carrier 680 in an up and down or vertically pulsating motion. It is contemplated the slots 665 and 679 can be aligned in other directions so as to provide a combination of side-to-side motion and a pulsating or up and down motion to the first and/or third bristle carriers.

As depicted in FIG. 7, upon operation of the toothbrush 602 and the drive shaft 616 preferably undergoing orbital motion, the first bristle carrier 660 undergoes a reciprocating side-to-side motion along a Z axis that is transverse to the longitudinal axis of the toothbrush and/or head, the second bristle carrier 670 undergoes an oscillating motion about an axis transverse to the longitudinal axis of the toothbrush 602 an/or head, and the third bristle carrier 680 undergoes reciprocating up and down or pulsating motion in a direction generally transverse to the longitudinal axis of the toothbrush and/or head (i.e., in a Y axis direction). The direction and type of motion of each of the bristle carrier 660, 670, and 680 is governed, in part, by the orientation and configuration of the engagement slots or apertures 666, 676, and 686 as well as the manner in which the bristle carriers are mounted to the toothbrush head.

Figure 8:
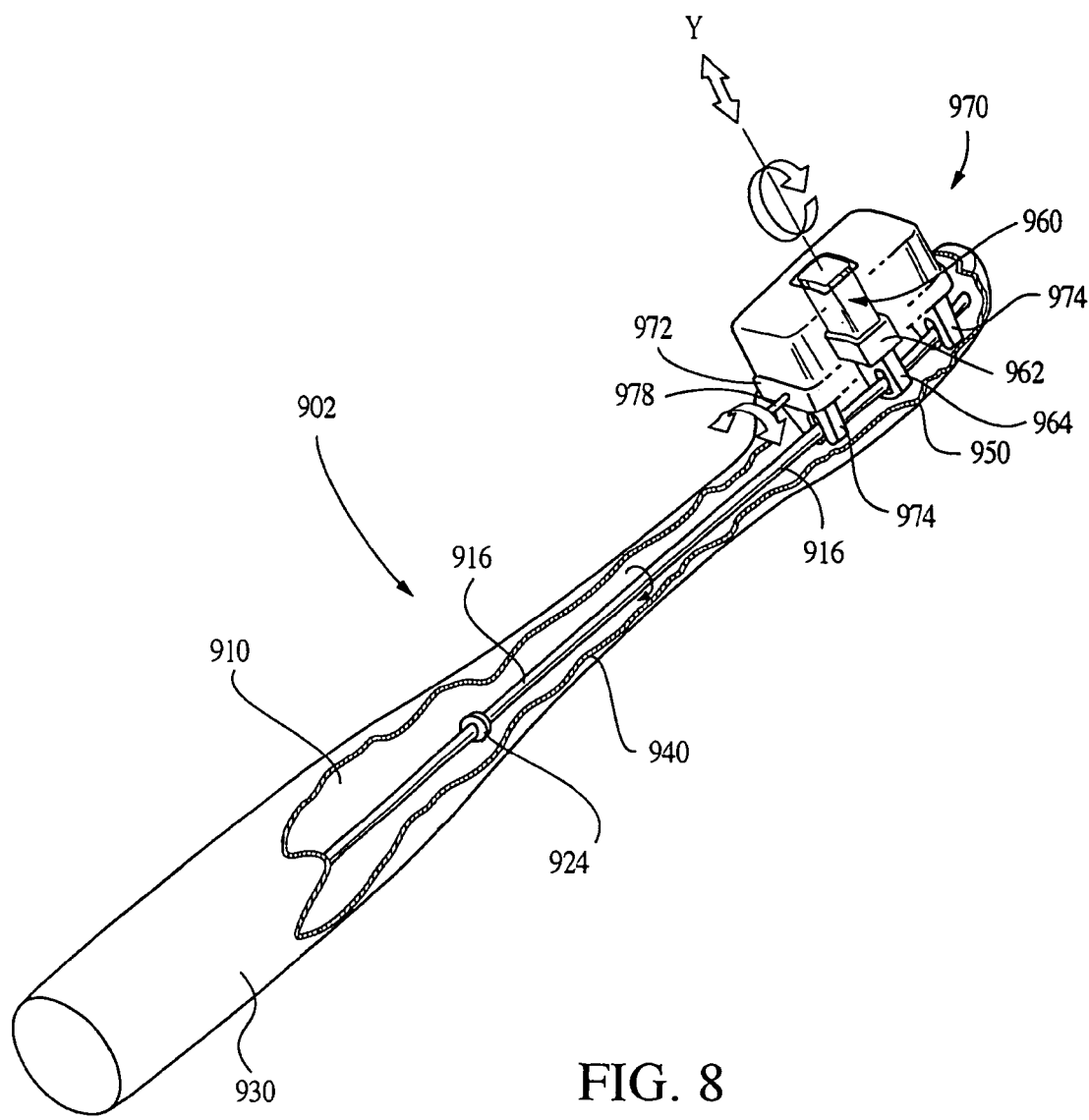
FIG. 8 is a perspective view of yet another preferred embodiment toothbrush in accordance with the present invention, wherein portions of the body, neck and head of the toothbrush have been removed for clarity.

FIG. 8 is a perspective view of yet another preferred embodiment toothbrush 902 in accordance with the present invention. The toothbrush 902 includes a body 910 having a handle 930, a head 950, and a neck 940 extending between the handle 930 and the head 950. Disposed within the interior of the body 910 is a drive shaft 916. The drive shaft 916 preferably undergoes orbital motion upon operation of the toothbrush 902. The drive shaft 916 preferably extends through a pivot member 924 and one or more collars of bristle carriers described in greater detail herein. As can be seen in FIG. 8, disposed on the head 950 is a first bristle carrier 960 having a base 962 that engages the drive shaft 916 via a collar 964. Also disposed on the head 950 is a second bristle carrier 970 having a base 972 with one or more corresponding collars 974 that engage the drive shaft 916. Most preferably, the second bristle carrier 970 includes an interior void or open region within which is slidably disposed the first bristle carrier 960 such that the second bristle carrier surrounds the first bristle carrier. Upon operation of the toothbrush 902 and orbital motion of the drive shaft 916, a variety of motions and combinations of motions may be imparted to the bristle carriers 960 and 970.

In the toothbrush embodiment 902, the second bristle carrier 970 undergoes an oscillating motion about a longitudinal axis that passes through one or more pins 978 extending from the base 972 of the carrier 970. The pins 978 cooperate with holes (not shown) in the toothbrush head to guide the bristle carrier 970 in this motion. The first bristle carrier 960 is preferably operatively connected to the drive shaft 916 that passes under a portion of the second bristle carrier 970 to the first bristle carrier 960 so that the first bristle carrier 960 undergoes the same orbital motion as the drive shaft. Alternatively, it is contemplated that the bristle carrier 960 can engage the drive shaft 916 and be mounted in any one of the manners previously described herein.

Figure 9A:
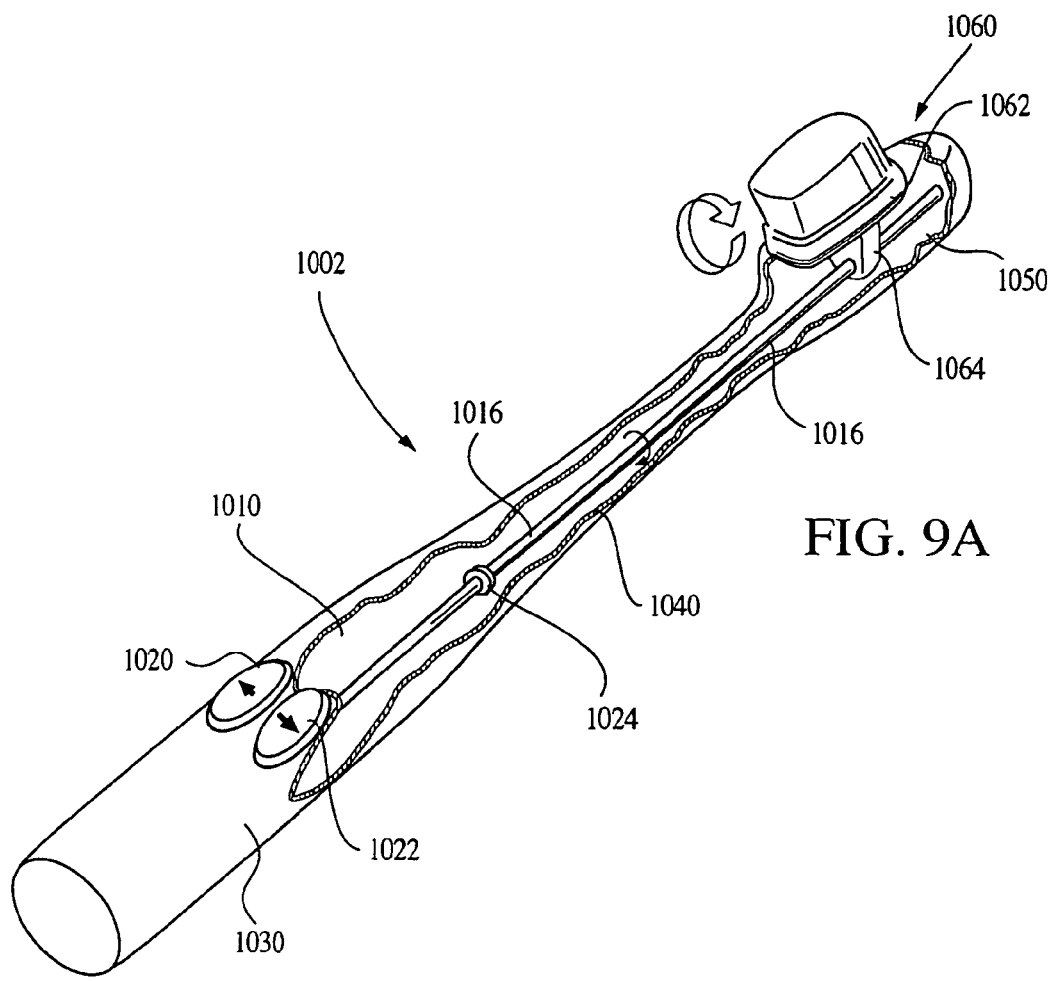
FIG. 9A is a perspective view of yet another preferred embodiment toothbrush in accordance with the present invention, wherein portions of the body, neck and head of the toothbrush have been removed for clarity.

FIG. 9A is a perspective view of yet another preferred embodiment toothbrush 1002 in accordance with the present invention. The preferred embodiment toothbrush 1002 includes a body 1010 having a pair of switches 1020 and 1022, a handle 1030, a head 1050, and a neck 1040 extending between the handle 1030 and the head 1050. Disposed within the interior of the body 1010 is a drive shaft 1016. The drive shaft preferably undergoes orbital motion upon operation of the toothbrush 1002. The drive shaft 1016 preferably extends through a pivot member 1024. Disposed on the brush head 1050 is a first bristle carrier 1060 having a base 1062 and a collar 1064 extending therefrom. The bristle carrier 1060 is fixedly connected to the drive shaft 1016. The toothbrush 1002 utilizes a pair of electrical switches 1020 and 1022 to selectively reverse the direction of a motor and drive train (not shown) disposed within the handle 1030, and thus also reverse the direction of movement of the bristle carrier 1060. Upon activation of the toothbrush 1002, for instance by actuation of switch 1020, the drive shaft 1016 undergoes orbital motion in, for example, a clockwise direction. Upon actuation of the switch 1022, the direction of motion is reversed such that the drive shaft 1016 undergoes orbital motion in, for example, a counter clockwise direction. It is contemplated that the two switches 1020 and 1022 can be combined into a single switch.

Figure 9B:
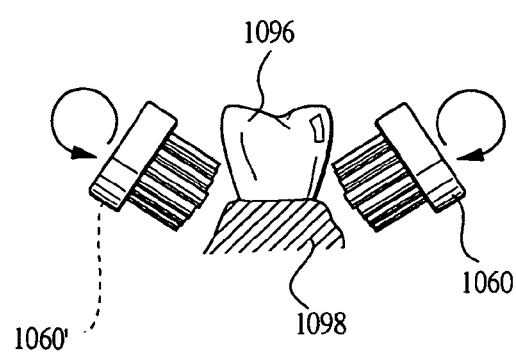
FIG. 9B is a schematic view of a brushing operation using the preferred embodiment toothbrush depicted in FIG. 9A.

FIG. 9B is a detailed view of a brushing operation using the preferred embodiment toothbrush 1002 shown in FIG. 9A. FIG. 9B illustrates a tooth 1096 extending from a region of gum 1098. FIG. 9B illustrates reversal of motion or change in direction of sweeping of the bristle carrier 1060 against the outer surface of the tooth 1096 and gum 1098. Specifically, the direction of motion of the bristle carrier 1060 may be changed or reversed by activation of the appropriate switch, i.e., switch 1020 or switch 1022. For instance, upon activation of switch 1020, the bristle carrier 1060 may move in the direction shown in FIG. 9B such that it sweeps upward from the outer surface of the gum and further upward along the outer surface of the tooth 1096 (shown as the right hand side of the tooth and gum in FIG. 10B). In contrast, upon activation of switch of 1022, the direction of motion changes such that the bristle carrier 1060' moves so that it also sweeps upward along the opposite outer surface of the gum 1098 and the tooth 1096, (shown as the left hand side in FIG. 9B).

FIG. 10A illustrates a perspective view of another preferred embodiment toothbrush 1102 having a plurality of bristle carriers in accordance with the present invention. The toothbrush 1102 comprises a body 1110 having a switch (not shown), a handle 1130, a head 1150, and a neck 1140 extending between the handle 1130 and the head 1150. Disposed within the interior region of the body 1110 is an electric motor 1112, an orbital motion assembly 1114, and a drive shaft 1116. The assembly 1114 comprises a disk that is operatively coupled to the electric motor so that the disk rotates about the central axis of the motor. Gearing (not shown) may be provided between the disk and the motor to vary the rotational speed of the disk. The shaft 1116 is eccentrically coupled to the disk so that the shaft undergoes an orbital motion when the motor is operating. A pivot member 1124 is provided. Other arrangements can be used in place of the ball and socket arrangement to provide a pivoting member, as previously discussed. The drive shaft 1116 preferably undergoes orbital motion.

FIG. 10B illustrates the motor and drive mechanism of the toothbrush 1102 depicted in FIG. 10A. FIG. 10B further illustrates another feature of the present invention, the use of a cam member 1118 disposed on the orbital motion drive shaft 1116. In this configuration, a hinged member 1115 is used to affix the drive shaft 1116 to the disk of the orbital motion drive assembly 1114. The hinged member 1115 prevents rotation of the shaft 1116 relative to the disk of assembly 1114. That is, the rotation of the drive shaft 1116 corresponds with the rotation of the disk 1114. As can be seen in FIG. 10B, the cam member 1118 is eccentrically affixed or disposed about the shaft 1116 such that the outer surface of member 1118 sweeps a circular path designated as J in FIG. 10B. It will be appreciated that the radius of circular path J is greater than the corresponding circular path through which a corresponding surface of the drive shaft 1116 sweeps.

The collection of bristle carriers includes a first bristle carrier 1160 disposed at a distal-most end 1152 and a second bristle carrier 1170 disposed between the first bristle carrier and the handle. The first bristle carrier 1160 can be arranged and configured as previously described with respect to FIGS. 2A and 2C. The first bristle carrier 1160 includes a base 1162 having a collar 1164 similar to the collar 164 shown in FIGS. 2A and 2C. The first bristle carrier 1160 also preferably includes a pin 1163. The second bristle carrier 1170 includes a base 1172 also provided with a collar 1174. The second bristle carrier 1170 preferably has one or more slots 1175 that engage one more longitudinally directed stationary or fixed pins (not shown) that are embedded in the head 1150. The slots 1175 and pins cooperate to guide the second bristle carrier 1170 in a reciprocating side-to-side motion transverse to the longitudinal axis of the toothbrush and/or head. Each of the collars 1164, 1174 defines an engagement slot or aperture as previously described. Upon operation of the toothbrush 1102 and orbital motion of the drive shaft 1116, the shaft operatively engages each of the collars of the first and second bristle carriers to impart motion thereto. In the embodiment depicted in FIG. 10A, the first bristle carrier 1160 can undergo the same motion as bristle carrier 160 of FIG. 2A, i.e. oscillation about a Y axis, and the second bristle carrier 1170 undergoes reciprocating motion along a Z axis of the toothbrush 1102 that is transverse to the longitudinal axis (e.g., X axis) of the toothbrush 1102 and/or the head of the toothbrush.

FIG. 10C illustrates the significance of the use of the cam member 1118. In the toothbrush 1102, the cam member 1118 engages the second bristle carrier 1170. The use of the cam member 1118 imparts a motion to that bristle carrier having a greater amplitude or extent of travel as compared to if the member 1118 is not used, and engagement is solely between the shaft 1116 undergoing orbital motion and the carrier 1170. The cam member can be provided as a bend in the shaft 1116, a bead, or other suitable structure.

Figure 11:
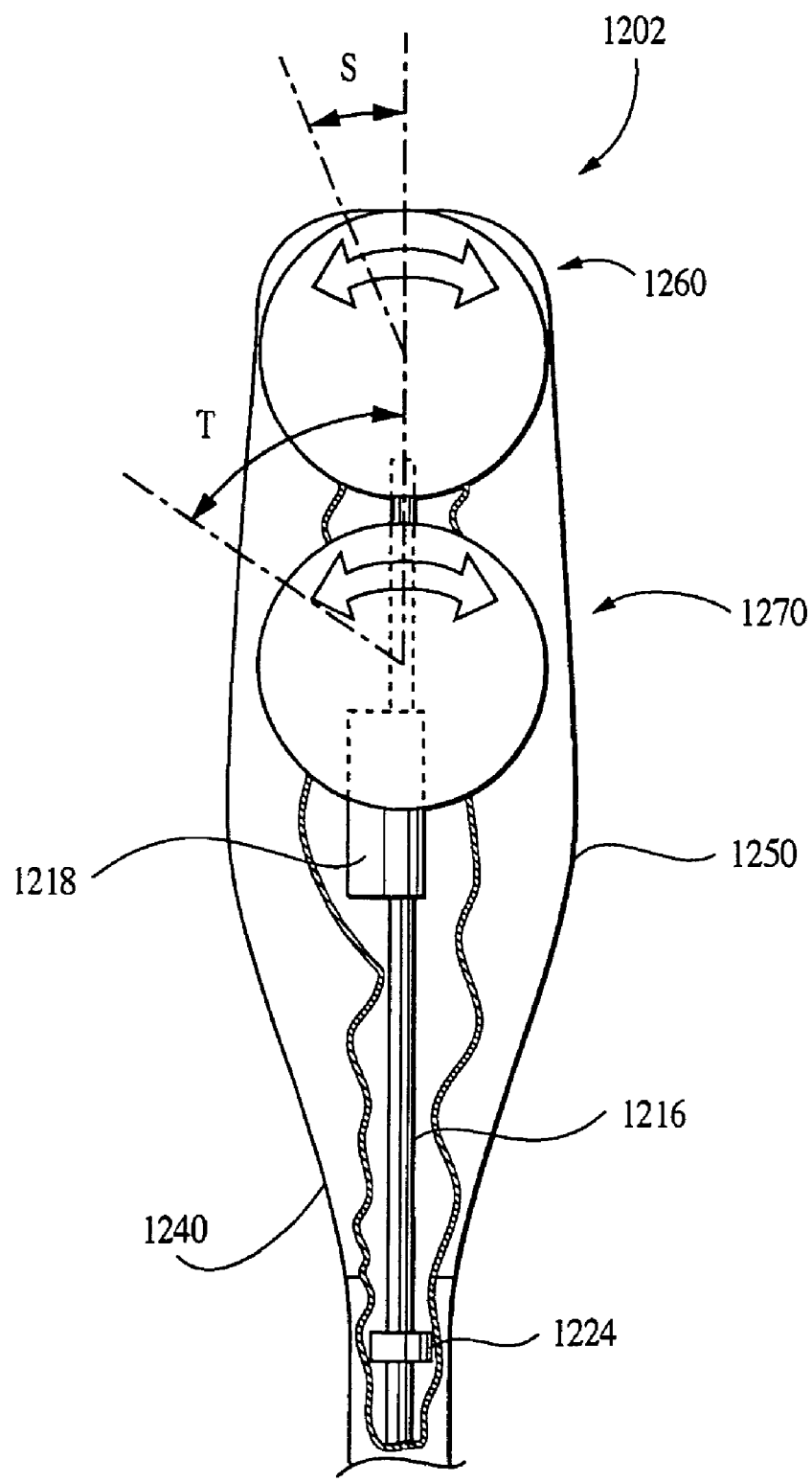
FIG. 11 is a planar, schematic view of a head and neck of another preferred embodiment toothbrush in accordance with the present invention.

FIG. 11 is a planar, schematic view of a head 1250 and neck 1240 of another preferred embodiment toothbrush 1202 in accordance with the present invention. The toothbrush 1202 comprises a first bristle carrier 1260 and a second bristle carrier 1270, both of which undergo an oscillating motion about a Y axis, similar to the bristle carrier 160 shown in FIGS. 2A and 2C. However, the toothbrush of FIG. 11 utilizes a cam member 1218 affixed on a shaft 1216 which extends through a pivot member 1224 analogous to the drive mechanism depicted in FIG. 10B. The use of the cam member 1218 increases the amplitude of the angular motion through which the second bristle carrier 1270 undergoes. The arc T shown in FIG. 11 through which the bristle carrier 1270 moves, is from about 25° to about 45°. The arc S through which the bristle carrier 1260 moves is about 10° to about 15° C.

FIG. 12A illustrates a perspective view of another preferred embodiment toothbrush 1302 having a plurality of bristle carriers in accordance with the present invention. The toothbrush 1302 comprises a body 1310 having a switch (not shown), a handle 1330, a head 1350, and a neck 1340 extending between the handle 1330 and the head 1350. Disposed within the interior region of the body 1310 is an electric motor 1312, an orbital motion assembly 1314, and a drive shaft 1316. The assembly 1314 comprises a disk that is operatively coupled to the electric motor so that the disk rotates about the central axis of the motor. Gearing (not shown) may be provided between the disk and the motor to vary the rotational speed of the disk. The shaft 1316 is eccentrically coupled to the disk so that the shaft undergoes an orbital motion when the motor is operating. A pivot member 1324 is provided. Other arrangements can be used in place of the ball and socket arrangement to provide a pivoting member, as previously discussed. The drive shaft 1316 preferably undergoes orbital motion. The collection of bristle carriers includes a first bristle carrier 1360 disposed at a distal-most end 1352 and a second bristle carrier 1370 disposed between the first bristle carrier and the handle. The second bristle carrier 1370 can be arranged and configured as the bristle carrier 160 previously described with respect to FIGS. 2A and 2C. The second bristle carrier 1370 includes a base 1372 having a collar 1374 similar to the collar 164 shown in FIGS. 2A and 2C. The collar 1374 defines an aperture or slot 1376. The second bristle carrier 1370 also preferably includes one or more radially directed slots 1375 and a pin (not shown). The first bristle carrier 1360 includes a base 1362 provided with a cam member 1363, preferably located at the center of the first bristle carrier 1360. The first bristle carrier 1360 preferably has one or more slots 1365 that engage one more stationary or fixed pins (not shown) that are embedded in the head 1350. The slots 1365 and pins cooperate to guide the first bristle carrier 1360 in a reciprocating front-to-rear motion parallel to the longitudinal axis of the toothbrush and/or head. Upon operation of the toothbrush 1302 and orbital motion of the drive shaft 1316, the shaft operatively engages the aperture 1376 of the second bristle carrier 1370 to impart motion thereto. And, the drive shaft 1316 engages cam surfaces of the cam member 1363, as described in greater detail herein, to impart motion to the first bristle carrier 1360. In the embodiment depicted in FIG. 12A, the second bristle carrier 1370 can undergo the same motion as bristle carrier 160 of FIG. 2A, and the first bristle carrier 1360 undergoes reciprocating motion along an X axis of the toothbrush 1302 that is generally or substantially parallel to the longitudinal axis (e.g., X axis) of the toothbrush 1302 and/or the head of the toothbrush.

FIG. 12B is an elevational side view of the first bristle carrier 1360 illustrating its engagement with the drive shaft 1316. As shown in FIG. 12B, the bristle carrier 1360 comprises a plurality of bristles 1361 extending from and supported by the base 1362. Extending from the underside of the base 1362 is the cam member 1363. The cam member 1363 includes an upper outwardly extending arm 1363*a*, and a lower outwardly extending arm 1363*b*. The arms 1363*a* and 1363*b* periodically engage the drive shaft 1316 as it undergoes orbital motion. Specifically, in the embodiment depicted in FIGS. 12A and 12B, the upper arm 1363*a* provides a first cam surface along the underside of the arm 1363*a* that momentarily contacts the drive shaft 1316 as the shaft sweeps or travels through its path of motion. Similarly, the lower arm 1363*b* provides a second cam surface facing upwards (and facing the underside of the upper arm 1363*a*) that momentarily contacts the drive shaft 1316 as the shaft sweeps or travels through its path of motion. FIG. 12B further illustrates that the arms 1363*a* and 1363*b* are preferably oriented at an acute angle with respect to the longitudinal axis of the toothbrush. The preferred inclination of the corresponding first and second cam surfaces provided by the arms 1363*a* and 1363*b*, in conjunction with the previously described slot 1365 and pin arrangement, results in the bristle carrier 1360 reciprocating along the X axis of the toothbrush upon the drive shaft undergoing orbital motion.

It will be understood that the orientation and inclination of the arms 1363*a* and 1363*b* may be reversed so that the arms extend in a downwardly direction. Furthermore, the arrangement of the bristle carriers 1360 and 1370 may be changed such that the bristle carrier 1370 is disposed adjacent the distal-most end 1352 of the toothbrush. In this arrangement, the cam member 1363 of the bristle carrier 1360 would be disposed at a suitable location along the underside of the base 1362 such that the drive shaft 1316 may extend past the member 1363 to the other bristle carrier 1370. In this arrangement, a secondary drive component extending from the drive shaft 1316 could be used to engage the cam member 1363.

It will be appreciated that in all of the embodiments of the present invention, one or more groups of static bristles or other cleaning members may be provided in conjunction with the moving bristles. It may, in many instances, be preferred to provide a collection of static bristles on the toothbrush head. For example, static bristles may be disposed in a gap between bristle carriers 1400 of FIG. 7, or may completely encircle the bristle carriers. Static bristles may also be disposed at the distal-most end of the head 1410 of FIG. 7, and/or at the rearward-most portion of the head and/or adjacent the sides of the toothbrush head. Further examples of static bristles that may be used with the present invention are described in U.S. patent application Ser. No. 10/274,700 and U.S. Pat. No. 6,360,395. Moving or static elastomeric bristles, formed for example from a thermoplastic elastomer or rubber, can also be provided on the moving bristle carriers or the toothbrush head. An example of one arrangement is described in U.S. Pat. No. 6,371,294.

While brush head embodiments of the present invention have been illustrated for simplicity with tufts of bristles that extend in a direction substantially perpendicular to the longitudinal axis of the head from which they extend, it is contemplated that the static and/or movable bristles might be arranged differently to compliment or further enhance the static bristles or the motion of the movable bristles. Some or all of the bristles might extend in a direction that forms an acute angle with a top surface of a bristle holder and may extend in a forward or rearward direction. In another embodiment, some of the bristles might extend outwardly away from the head, in another direction, again forming an acute angle with respect to the top surface of the bristle holder. Examples of other suitable bristle arrangements are described in U.S. Pat. Nos. Des. 330,286, Des. 434,563; 6,006,394; 4,081,876; 5,046,213; 5,335,389; 5,392,483; 5,446,940; 4,894,880; and International Publication No. WO99/23910.

The toothbrushes of the present invention may be formed from a wide array of polymers. In the following description of the preferred polymer materials for use herein, the abbreviations that are commonly used by those of skill in the art to refer to certain polymers appear in parentheses following the full names of the polymers. The polymer is preferably polypropylene ("PP"), or may be selected from the group consisting of other commercially available materials, such as polystyrene ("PS"), polyethylene ("PE"), acrylonitrile-styrene copolymer ("SAN"), and cellulose acetate propionate ("CAP"). These materials may be blended with one or more additional polymers including a thermoplastic elastomer ("TPE"), a thermoplastic olefin ("TPO"), a soft thermoplastic polyolefin (e.g., polybutylene), or may be selected from other elastomeric materials, such as etheylene-vinylacetate copolymer ("EVA"), and ethylene propylene rubber ("EPR"). Examples of suitable thermoplastic elastomers herein include styrene-ethylene-butadiene-styrene ("SEBS"), styrene-butadiene-styrene ("SBS"), and sterene-isoprene-styrene ("SIS"). Examples of suitable thermoplastic olefins herein include polybutylene ("PB"), and polyethylene ("PE"). Techniques known to those of skill in the art, such as injection molding, can be used to manufacture the toothbrush of the present invention.

The present invention has been described with reference to particular preferred embodiments. Modifications and alterations may be made to these embodiments within the scope of the present invention. For example, certain combinations of bristle carriers have been described herein. It will be appreciated that the bristle carriers can be rearranged and the bristle carrier of one embodiment substituted for that of another. For instance, the bristle carrier 660 of FIG. 7 might be substituted for the bristle carrier 160 of FIG. 2A or bristle carrier 260 of FIG. 3. Further, while some bristle carriers may have a slot that engages a pin on the toothbrush head to guide the movement of the bristle carrier, it will be appreciated that these features can be reversed so that the pin is disposed on the bristle carrier and the slot is disposed on the head, and further that other structures known in the art can be used to guide the motion of any of the bristle carriers described herein. It is intended that all such modifications and alterations are included insofar as they come within the scope of the appended claims or equivalents thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush, comprising:
   a handle having an electric motor;
   a head;
   a first bristle carrier having a plurality of bristles and a second bristle carrier having a plurality of bristles, wherein said first and second bristle carriers are disposed on said head;
   wherein said first and second bristle carriers are generally transverse to the longitudinal axis of said head;
   wherein said electric motor is operatively connected to said first and second bristle carriers;
   wherein said first bristle carrier reciprocates in a side-to-side motion transverse to the longitudinal axis of said head, and said second bristle carrier reciprocates in an up-and-down direction transverse to the longitudinal axis of said head generally transverse to the direction of movement of the first bristle carrier; and
   wherein a first plurality of static bristles are disposed in between said first and second bristle carriers.

2. The electric toothbrush of claim 1, wherein said electric motor is operatively connected to a shaft, wherein operation of said electric motor moves said shaft in an orbital motion.

3. The electric toothbrush of claim 1, wherein at least one said bristle carrier has elastomeric bristles.

4. The electric toothbrush of claim 1, wherein said static bristles comprise elastomeric bristles.

5. The electric toothbrush of claim 1, wherein at least one said bristle carrier has elastomeric bristles and said static bristles comprise elastomeric bristles.

6. The electric toothbrush of claim 1, wherein a second plurality of static bristles are disposed at a distal-most end of said head.

7. The electric toothbrush of claim 1, wherein said electric motor is operatively connected to a third bristle carrier.

8. The electric toothbrush of claim 1, wherein said first and second bristle carriers are elongated in a direction transverse to the longitudinal axis of said head.

9. An electric toothbrush, comprising:
   a handle having an electric motor;
   a head;
   a first bristle carrier having a plurality of bristles and a second bristle carrier having a plurality of bristles, wherein said first and second bristle carriers are disposed on said head;
   wherein said first and second bristle carriers are generally transverse to the longitudinal axis of said head;

wherein said electric motor is operatively connected to said first and second bristle carriers;

wherein the tips of the bristles of said first bristle carrier move in a side-to-side direction generally transverse to the longitudinal axis of said head and the tips of the bristles of said second bristle carrier move in an up-and-down direction generally transverse to the longitudinal axis of said head generally transverse to the direction of movement of the bristle tips of the first bristle carrier; and wherein static bristles are disposed at a distal-most end of said head.

10. The electric toothbrush of claim 9, wherein said electric motor is operatively connected to a shaft, wherein operation of said electric motor moves said shaft in an orbital motion.

11. The electric toothbrush of claim 9, wherein at least one said bristle carrier has elastomeric bristles and/or said static bristles comprise elastomeric bristles.

* * * * *

UNITED STATES PATENT AND TRADEMARK OFFICE
CERTIFICATE OF CORRECTION

PATENT NO. : 7,421,753 B2  Page 1 of 1
APPLICATION NO. : 11/410808
DATED : September 9, 2008
INVENTOR(S) : John Geoffrey Chan et al.

It is certified that error appears in the above-identified patent and that said Letters Patent is hereby corrected as shown below:

Column 15

Line 8, delete "arc" and insert -- are --.

Line 10, delete "clastomeric" and insert -- elastomeric --.

Signed and Sealed this

Fifth Day of January, 2010

David J. Kappos
*Director of the United States Patent and Trademark Office*